United States Patent
Braun et al.

(10) Patent No.: US 6,537,768 B1
(45) Date of Patent: Mar. 25, 2003

(54) DIAGNOSIS, PREVENTION AND TREATMENT OF ULCERATIVE COLITIS, AND CLINICAL SUBTYPES THEREOF, USING MICROBIAL UC PANCA ANTIGENS

(75) Inventors: Jonathan Braun, Tarzana, CA (US); Offer Cohavy, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/417,264

(22) Filed: Oct. 12, 1999

Related U.S. Application Data

(60) Division of application No. 09/041,889, filed on Mar. 12, 1998, now Pat. No. 6,033,864, which is a continuation-in-part of application No. 08/837,058, filed on Apr. 11, 1997, now Pat. No. 6,074,835.
(60) Provisional application No. 60/057,846, filed on Apr. 12, 1996.

(51) Int. Cl.[7] ............................................. G01N 33/564
(52) U.S. Cl. .................... 435/7.32; 435/7.21; 435/7.24; 435/7.95; 436/506; 436/508
(58) Field of Search ............................. 435/7.21, 7.24, 435/7.32, 7.95; 436/506, 508

(56) References Cited

U.S. PATENT DOCUMENTS 6,074,835 A * 6/2000 Braun et al. ................ 435/7.21

FOREIGN PATENT DOCUMENTS

WO 97/38713 * 10/1997

OTHER PUBLICATIONS

Pool et al, Gut, 34, 46–50, 1993.*

Provdjansky et al, J. Pediat. Gastroenterol. Nutr., 17, 193–197, 1993.*

Saxon et al, Jour. Allerg. Clin. Immunol., 86, 202–210, 1990.*

Eggena et al, FASEB Jour., 10, A1079, Abstract No. 463, 1996.*

* cited by examiner

Primary Examiner—David Saunders
(74) Attorney, Agent, or Firm—Campbell & Flores LLP

(57) ABSTRACT

The present invention relates to microbial UC pANCA antigens. The invention provides methods of diagnosing ulcerative colitis (UC) and methods of inducing tolerance in a pANCA-positive patient with UC using a histone H1-like antigen. The invention further provides methods of diagnosing UC and methods of inducing tolerance in a pANCA-positive patient with UC using a porin antigen. Methods of diagnosing UC and methods of inducing tolerance in a pANCA-positive patient with UC using a Bacteroides antigen also are provided.

10 Claims, 12 Drawing Sheets

Human Histone H1$^S$-1 (SEQ ID NO: 1)
SETAPAAPAAAPPAEKAPVKKKAAKKAGGTPRKASGPPVSELITKAVA
ASKERSGVSLAALKKALAAAGYDVEKNNSRIKLGLKSLVSKGTLVQTK
GTGASGSFKLNKKAASGEAKPKVKKAGGTKPKKPVGAAKKPKKAAG
GATPKKSAKKTPKKAKKPAAATVTKKVAKSPKKAKVAKPKKAAKSA
AKAVKPKAAKPKVVKPKKAAPKKK Human Histone H1$^S$-2 (SEQ ID NO: 2)
SETAPLAPTIPAPAEKTPVKKKAKKAGATAGKRKASGPPVSELITKAVA
ASKERSGVSLAALKKALAAAGYDVEKNNSRIKLGLKSLVSKGTLVQTK
GTGASGSFKLNKKAASGEGKPKAKKAGAAKPRKPAGAAKKPKKVAG
AATPKKSIKKTPKKVKKPATAAGTKKVAKSAKKVKTPQPKKAAKSPA
KAKAPKPKAAKPKSGKPKVTKAKKAAPKKK Human Histone H1$^S$-3 (SEQ ID NO: 3)
SETAPAETATPAPVEKSPAKKKATKKAAGAGAAKRKATGPPVSELITK
AVAASKERNGLSLAALKKALAAGGYDVEKNNSRIKLGLKSLVSKGTL
VQTKGTGASGSFKLNKKAASGEAKPKAKKAGAAKAKKPAGATPKKA
KKAAGAKKAVKKTPKKAKKPAAAGVKKVAKSPKKAKAAAKPKKAT
KSPAKPKAVKPKAAKPKAAKPKAAKPKAKKAAAKKK Human Histone H1$^S$-4 (SEQ ID NO: 4)
SETAPAAPAAPAPAEKTPVKKKARKSAGAAKRKASGPPVSELITKAVA
ASKERSGVSLAALKKALAAAGYDVEKNNSRIKLGLKSLVSKGTLVQTK
GTGASGSFKLNKKAASGEAKPKAKKAGAAKAKKPAGAAKKPKKATG
AATPKKSAKKTPKKAKKPAAAGAKKAKSPKKAKAAKPKKAPKSPA
KAKAVKPKAAKPKTAKPKAAKPKKAAAKKK Human Histone H1° (SEQ ID NO: 5)
TENSTSAPAAKPKRAKASKKSTDHPKYSDMIVAAIQAEKNRAGSSRQSI
QKYIKSHYKVGENADSQIKLSIKRLVTTGVLKQTKGVGASGSFRLAKS
DEPKKSVAFKKTKKEIKKVATPKKASKPKKAASKAPTKKPKATPVKKA
KKKLAATPKKAKKPKTVKAKPVKASKPKKAKPVKPKAKSSAKRAGK
KK Human Histone H1t (SEQ ID NO: 6)
SETVPAASASAGVAAMEKLPTKKRGRKPAGLISASRKVPNLSVSKLITE
ALSVSQERVGMSLVALKKALAAAGYDVEKNNSRIKLSLKSLVNKGILV
QTRGTGASGSFKLSKKVIPKSTRSKAKKSVSAKTKKLVLSRDSKSPKTA
KTNKRAKKPRATTPKTVRSGRKAKGAKGKQKQKSPVKARASKSKLTQ
HHEVNVRKATSKK

FIG. 1

NANUC-1

NANUC-2

π

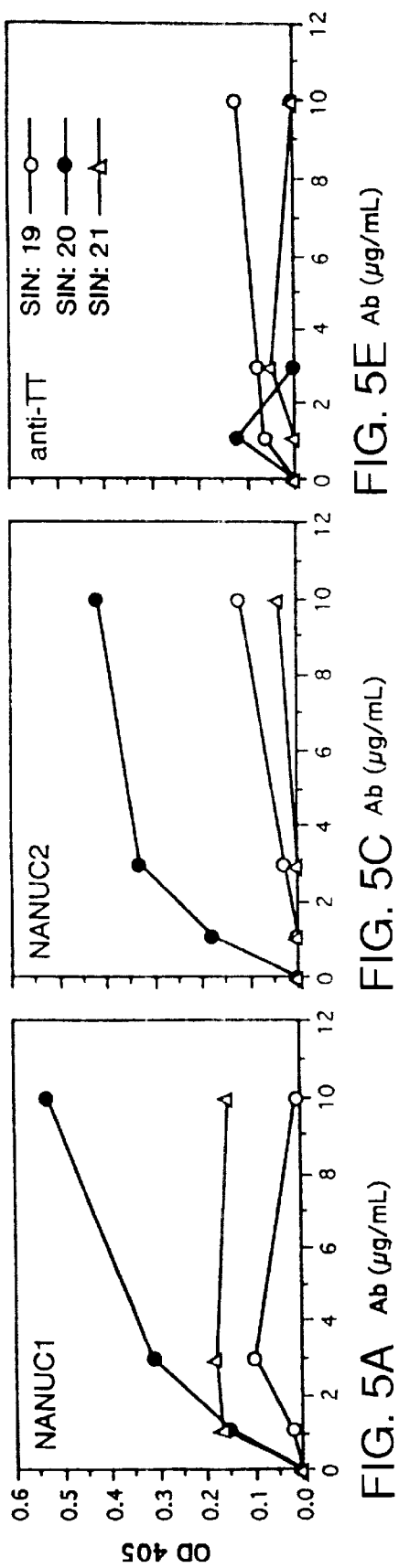

FIG. 6

| STRAIN | SOURCE | STOCK | MEDIUM | GROWTH |
|---|---|---|---|---|
| *Mycobacterium tuberculosis* (Erdman–Pathogenic) | ATCC #35801 | −70°C<br>8% Glycerol | Middlebrook 7H9 Medium with OADC Enrichment plus:<br>1g L–glutamine/L. and<br>1% Glycerol see ATCC#173 | ~3 weeks (18–21days), at 37°C with 5% $CO_2$ from $5x10^5$ cfu/ml to $1–2x10^8$ cfu/ml in 300ml volume/2L flask |
| *Mycobacterium bovis* (Pathogenic) | ATCC #19210 | −70°C<br>8% Glycerol | Middlebrook 7H9 Medium with OADC Enrichment plus:<br>1g L–glutamine/L. and<br>1% Glycerol see ATCC#173 | ~3 weeks (18–21days), at 37°C with 5% $CO_2$ from $5x10^5$ cfu/ml to $1–2x10^8$ cfu/ml in 300ml volume/2L flask |
| *Mycobacterium bovis* BCG (Attenuated) | ATCC #35734 | −70°C<br>8% Glycerol | Middlebrook 7H9 Medium with OADC Enrichment plus:<br>1g L–glutamine/L. and<br>1% Glycerol see ATCC#173 | ~3 weeks (18–21days), at 37°C with 5% $CO_2$ from $5x10^5$ cfu/ml to $1–2x10^8$ cfu/ml in 300ml volume/2L flask |
| *Mycobacterium smegmans 1–2c* (Non–pathogen) | Douglas Young, St. Mary's Hospital Medical School, London, UK. | −70°C<br>8% Glycerol | Middlebrook 7H9 Medium with OADC Enrichment plus:<br>1g L–glutamine/L. and<br>1% Glycerol see ATCC#173 | 3 days, at 37°C with 5% $CO_2$ on shaker at 180 rpm, from $5x10^5$ cfu/ml to $1–2x10^8$ cfu/ml in 300ml volume/4L flask |
| *Mycobacterium avium* (Opportunistic Pathogen) | ATCC #25291 | −70°C<br>8% Glycerol | Middlebrook 7H9 Medium with OADC Enrichment plus:<br>1g L–glutamine/L. and<br>1% Glycerol see ATCC#173 | ~3 weeks (18–21days), at 37°C with 5% $CO_2$ from $5x10^5$ cfu/ml to $1–2x10^8$ cfu/ml in 300ml volume/2L flask |
| *Mycobacterium avium Paratuberculosis* | ATCC #19698 | −70°C<br>8% Glycerol | Middlebrook 7H9 Medium with OADC Enrichment plus:<br>1g L–glutamine/L.<br>1% Glycerol, and 70μM $FeCl_3$<br>see ATCC#173 | ~3 weeks (18–21days), at 37°C with 5% $CO_2$ from $5x10^5$ cfu/ml to $1–2x10^8$ cfu/ml in 300ml volume/2L flask |
| *Mycobacterium avium paratuberculosis* "Linda" strain (Crohn's patient isolate) | ATCC #43015 | −70°C<br>8% Glycerol | Middlebrook 7H9 Medium with OADC Enrichment plus:<br>1g L–glutamine/L.<br>1% Glycerol, and 70μM $FeCl_3$<br>see ATCC#173 | ~3 weeks (18–21days), at 37°C with 5% $CO_2$ from $5x10^5$ cfu/ml to $1–2x10^8$ cfu/ml in 300ml volume/2L flask |

```
             1              15 16              30 31              45 46              60 61              75 76              90
1 N-term     MNKAELIDVLTTKMX SDR-----RQXTAXVE D-------------- --------------- --------------- --------------- --------------
2 214        MNKAELIDVLTQKLG SDR-----RQATAAVE NVVDTIVRAVHKGDS VTITGFGVFEQRR-- ------RAARVARN PRTGETVKVKPTSVP
3 H1.5       MSETAPAETATPAPV EKS-PAKKKATKKAA GAGAAKRKATGPPVS ELITKAVAASKERNG LSLAALKKALAAGGY DVEKNNSRIKLGLKS 91             105 106            120 121            135 136            150 151            165 166            180
1 N-term     -------------- --------------- --------------- --------------- --------------- ---------------
2 214        AFRPGAQFKAVVSGA QRLPAEGPAVKRGVG ASAAKKVAKKAPAKK ATKAAKKAATKAPAR KAATKAPAKKAATKA PAKKAVKKATKSPAKK
3 H1.5       LVSKGTLVQTKGTGA SGSFKLNKKAASGEA KPKAKKAGAAKAKKP AGATPKKAKKAAGAK KAVKKTPKKAKKPAA AGVKKVAKSPKKAKA 181            195 196            210 211            225 226            27
1 N-term     -------------- --------------- --------------- -- 27
2 214        VTKAVKTAVKASVR KAATKAPAKKAAAKR PATKAPAKATARRG RK 214
3 H1.5       AAKPKKATKSPAKPK AVKPKAAKPKAAKPK AAKPKAAKAKKAAAK KK 226
```

FIG. 8

Human histone H1a (H1.5):

```
  1 msetapaeta tpapvekspa kkkatkkaag agaakrkatg ppvselitka vaaskerngl
 61 slaalkkala aggydveknn sriklglksl vskgtlvqtk gtgasgsfkl nkkaasgeak
121 pkakkagaak akkpagatpk kakkaagakk avkktpkkak kpaaagvkkv akspkkakaa
181 akpkkatksp akpkavkpka akpkaakpka akpkaakakk aaakkk
```

M. tubeculosis 214 amino acid histone H1 homologue:

```
  1 mnkaelidvl tqklgsdrrq ataavenvvd tivravhkgd svtitgfgvf eqrrraarva
 61 rnprtgetvk vkptsvpafr pgaqfkavvs gaqrlpaegp avkrgvgasa akkvakkapa
121 kkatkaakka atkaparkaa tkapakkaat kapakkavka tkspakkvtk avkktavkas
181 vrkaatkapa kkaaakrpat kapakkatar rgrk
```

E. coli 323 amino acids outer membrane protein F precursor:

```
  1 mkskvlalli pallaagaah aaevynkdgn kldlygkvdg lhyfsdnsak dgdqsyarlg
 61 fkgetqindq ltgygqweyn iqanntessk nqswtrlafa glkfadygsf dygrnygvmy
121 diegwtdmlp efggdsytna dnfmtgrang vatyrntdff glvnglnfav qyqgnnegas
181 ngqegtnngr dvrhengdgw glsttydlgm gfsagaayts sdrtndqvnh taaggdkada
241 wtaglkydan niylatmyse trnmtpfgds dyavanktqn fevtaqyqfd fglrpavsfl
301 mskgrdlhaa ggadnpagvd dkd
```

E. coli 377 amino acids outer membrane protein F precursor:

```
  1 mkskvlalli pallaagaah aaevynkdgn kldlygkvdg lhyfsdnsak dgdqsyarlg
 61 fkgetqindq ltgygqweyn iqanntessk nqswtrlafa glkfadygsf dygrnygvmy
121 diegwtdmlp efggdsytna dnfmtgrang vatyrntdff glvnglnfav qyqgnnegas
181 ngqegtnngr dvrhengdgw glsttydlgm gfsagaayts sdrtndqvnh taaggdkada
241 wtaglkydan niylatmyse trnmtpfgds dyavanktqn fevtaqyqfd fglrpavsfl
301 mskgrdlhaa ggadnpagvd dkdlvkyadi gatyyfnknm styvdykinl ldeddsfyaa
361 ngistddiva lglvyqf
```

E. coli 367 amino acids outer membrane protein c precursor:

```
  1 mkskvlalli pallaagaah aaevynkdgn kldlygkvdg lhyfsdnkdv dgdqtymrlg
 61 fkgetqvtdq ltgygqweyq iqgnsaenen nswtrvafag lkfqdvgsfd ygrnygvvyd
121 vtswtdvlpe fggdtygsdn fmqqrgnfga tyrntdffgl vdglnfavqy qgkngnpsge
181 gftsgvtnng rdalrqngdg vggsitydye gfgiggaiss skrtdaqnta ayigngdrae
241 tytgglkyda nniylaaqyt qtynatrvgs lgwankaqnf eavaqyqfdf glrpslaylq
301 skgknlgrgy ddedilkyvd vgatyyfnkn mstyvdykin llddnqftrd agintdniva
361 lglvyqf
```

FIG. 10

```
         1        15 16              30 31              45 46              60 61              75 76              90
N        ----------------- ----------------- ----------------- ----------------- ----------------- -----------------
323      ----------------- -----AEVYNKDGN    KLDLYGKVDG------- ----------------- ----------------- -----------------
hl.5     MKSKVLALLIPALLA   AGAAHAAEVYNKDGN   KLDLYGKVDGLHYFS   DNSAKDGDQSYARLG   FKGETQINDQLTGYG   QWEYNIQANNTESSK 91       105 106             120 121             135 136             150 151             165 166             180
N        ----------------- ----------------- ----------------- ----------------- ----------------- -----------------
323      ----------------- -----MSETA        PAETATPAPVEKSPA   KKKATKKAAGAGAAK   RKATGPPVSELITKA   VAASKERNGLSLAAL   KKALAAGGYDVEKNN
hl.5     NQSWTRLAFAGLKFA   DYGSFDYGRNYGVMY   DIEGWTDMLPEFGGD   SYTNADNFMTGRANG   VATYRNTDFFGLVNG   LNFAVQYQGNNEGAS 181      195 196             210 211             225 226             240 241             255 256             270
N        ----------------- ----------------- ----------------- ----------------- ----------------- -----------------
323      SRIKLGLKSLVSKGT   LVQTKGTGASGSFKL   NKKAASGEAKPKAKK   AGAAKAKKPAGATPK   KAKKAAGAKKAVKKT   PKKAKKPAAAGVKKV
hl.5     NGQEGTNNGRDVRHE   NGDGWGLSTTYDLGM   GFSAGAAYTSSDRTN   DQVNHTAAGGDKADA   WTAGLKYDANNIYLA   TMYSETRNMTPFGDS 271      285 286             300 301             315 316
N        ----------------- ----------------- -----------------
323      AKSPRKAKAAAKPKK   ATKSPAKPKAVKPKA   AKPKAAKPKAAKPKA   AKAKKAAAAKKK----
hl.5     DYAVANKTQNFEVTA   QYQFDFGLRPAVSFL   MSKGRDLHAAGGADN   PAGVDDKD
```

FIG. 11

DIAGNOSIS, PREVENTION AND TREATMENT OF ULCERATIVE COLITIS, AND CLINICAL SUBTYPES THEREOF, USING MICROBIAL UC PANCA ANTIGENS

This application is a division of application Ser. No. 09/041,889, filed Mar. 12, 1998, now issued as U.S. Pat. No. 6,033,864, which is a continuation-in-part of application Ser. No. 08/837,058, filed Apr. 11, 1997, now issued as U.S. Pat. No. 6,074,835, the entire contents of which are incorporated herein by reference and which claims priority to application Ser. No. 08/630,671, filed Apr. 12, 1996, which was converted to provisional application No. 60/057,846 filing date Apr. 12, 1996, now abandoned.

ACKNOWLEDGMENT

This work was supported by grant number DK46763 awarded by the National Institutes of Health and by grant number GM08042 awarded by the National Institutes of Health. The United States government has certain rights in this invention.

BACKGROUND OF THE INVENTION

1. Field of the Invention

The invention relates generally to the fields of immunology and inflammatory bowel disease and more specifically to the diagnosis and treatment of a clinical subtype of ulcerative colitis.

2. Background Information

Inflammatory bowel disease (IBD) is the collective term used to describe two gastrointestinal disorders of unknown etiology: Crohn's disease (CD) and ulcerative colitis (UC). The course and prognosis of ulcerative colitis, which occurs world-wide and is reported to afflict as many as two million people, varies widely. Onset of ulcerative colitis is predominantly in young adulthood with diarrhea, abdominal pain, and fever the three most common presenting symptoms. The diarrhea may range from mild to severe and often is accompanied by bleeding. Anemia and weight loss are additional common signs of UC. Ten percent to fifteen percent of all patients with inflammatory bowel diseases such as UC will require surgery over a ten year period. In addition, patients with UC are at increased risk for the development of intestinal cancer. Reports of an increasing occurrence of psychological problems, including anxiety and depression, are perhaps not surprising symptoms of what is often a debilitating disease that strikes people in the prime of life.

Unfortunately, the available therapies for ulcerative colitis are few, and both diagnosis and treatment have been hampered by a lack of knowledge regarding the etiology of the disease. What is clear, however, is that the pathogenesis of ulcerative colitis involves immune-mediated damage to the intestinal mucosa. Autoantibodies, specifically antibodies against cytoplasmic components of neutrophils (pANCA), have been reported in 68–80% of patients with ulcerative colitis, further supporting a role for immune dysregulation in this disease. However, the antigens recognized by these pANCA autoantibodies, which would be useful in diagnosing and treating UC patients have, to date, escaped identification.

In other inflammatory bowel diseases such as Crohn's disease, bacteria have been implicated in the initiation or progression of the disease. That microbes can play a role in Crohn's disease is supported, for example, by the efficacy of antibiotics and diet in mitigating disease in some Crohn's patients. However, until now a role for microbes or microbial antigens in the immune dysregulation producing UC has not been suspected. Such microbial antigens can be the original inducers of the disease-related immune response in UC and, as such, can contain displayed B-cell epitopes that react especially effectively with UC pANCA autoantibodies. As a consequence, these microbial antigens can increase the level of UC serodetection from its current level of 60–70% with the fixed neutrophil assay. Such microbial antigens also can bear a disease related T-cell epitope and, as likely original inducers of the disease-related immune response, can be particularly effective tolerogenic antigens for treating UC patients.

Thus, there is a need for identification and isolation of UC pANCA target antigens, including antigens of microbial origin such as those expressed in colonic bacteria of UC patients. Such antigens would be useful for diagnosing and treating the large population of UC patients that have pANCA autoantibodies. The present invention satisfies this need by providing the histone H1 UC pANCA target antigen and additional UC pANCA microbial antigens. Related advantages are provided as well.

SUMMARY OF THE INVENTION

The present invention provides methods of diagnosing ulcerative colitis (UC) by obtaining a sample from a subject suspected of having inflammatory bowel disease; contacting the sample with a histone H1-like antigen, or pANCA-reactive fragment thereof, under conditions suitable to form a complex of histone H1-like antigen, or pANCA-reactive fragment thereof, and antibody to histone H1-like antigen; and detecting the presence or absence of the complex, where the presence of the complex indicates that the subject has ulcerative colitis. A histone H1-like antigen useful in these methods can be, for example, a protein immunoreactive with NANUC-2 and having an amino acid sequence having at least 65% amino acid identity with SEQ ID NO: 27.

The invention also provides methods of inducing tolerance in a pANCA-positive patient with UC by administering to the patient an effective dose of a histone-like H1 antigen, or tolerogenic fragment thereof. Such a histone H1-like antigen can be, for example, a protein immunoreactive with NANUC-2 and having an amino acid sequence having at least 65% amino acid identity with SEQ ID NO: 27.

The present invention also provides a composition of histone H1-like antigen, or tolerogenic fragment thereof, combined with a tolerogizing molecule. In such a composition, a histone H1-like antigen can be, for example, a protein immunoreactive with NANUC-2 and having an amino acid sequence having at least 65% amino acid identity with SEQ ID NO: 27.

In addition, the present invention provides methods of UC by obtaining a sample from a subject suspected of having inflammatory bowel disease; contacting the sample with a porin antigen, or pANCA-reactive fragment thereof, under conditions suitable to form a complex of porin antigen, or pANCA-reactive fragment thereof, and antibody to porin antigen; and detecting the presence or absence of the complex, where the presence of the complex indicates that the subject has ulcerative colitis. A porin antigen useful in these methods can be, for example, a protein immunoreactive with NANUC-2 and having at least 65% amino acid identity with SEQ ID NO: 28, SEQ ID NO: 29 or SEQ ID NO: 30.

The invention also provides methods of inducing tolerance in a pANCA-positive patient with UC by administering to the patient an effective dose of a porin antigen, or tolerogenic fragment thereof. A porin antigen useful in these methods can be, for example, a protein immunoreactive with NANUC-2 and having at least 65% amino acid identity with SEQ ID NO: 28, SEQ ID NO: 29 or SEQ ID NO: 30.

In addition, there is provided a porin antigen, or tolerogenic fragment thereof, combined with a tolerogizing molecule. In a composition of the invention, a porin antigen can be, for example, a protein immunoreactive with NANUC-2 and having at least 65% amino acid identity with SEQ ID NO: 28, SEQ ID NO: 29 or SEQ ID NO: 30.

The present invention further provides methods of diagnosing UC by obtaining a sample from a subject suspected of having inflammatory bowel disease; contacting the sample with a Bacteroides antigen, or pANCA-reactive fragment thereof, under conditions suitable to form a complex of Bacteroides antigen, or pANCA-reactive fragment thereof, and antibody to Bacteroides antigen; and detecting the presence or absence of the complex, where the presence of the complex indicates that the subject has ulcerative colitis. A Bacteroides antigen useful in these methods can be, for example, a *Bacteroides cecae* protein immunoreactive with NANUC-2 and having a molecular weight of about 100 kDa by SDS-PAGE electrophoresis.

The invention also provides methods of inducing tolerance in a pANCA-positive patient with UC by administering to the patient an effective dose of a Bacteroides antigen, or tolerogenic fragment thereof. Such a Bacteroides antigen useful in these methods can be, for example, A *Bacteroides cecae* protein immunoreactive with NANUC-2 and having a molecular weight of about 100 kDa by SDS-PAGE electrophoresis.

Additionally, the invention provides a composition containing a Bacteroides antigen, or a tolerogenic fragment thereof, combined with a tolerogizing molecule. A *Bacteroides cecae* protein immunoreactive with NANUC-2 and having a molecular weight of about 100 kDa by SDS-PAGE electrophoresis is an example of a Bacteroides antigen useful in a composition of the invention.

Further provided herein are methods for identifying an agent useful for treating UC. The methods involve obtaining a sample of enteric bacteria from a patient with UC; isolating from the sample a bacterial species that expresses a pANCA-reactive antigen; contacting the bacterial species with an agent; and assaying for the reduced growth or viability of the bacterial species, where the reduced growth or viability of the bacterial species indicates that the agent is an agent useful for treating UC. Enteric bacterial species useful in these methods can be, for example, from the genera of Mycobacteria, Escherichia or Bacteroides.

BRIEF DESCRIPTION OF THE DRAWINGS

FIG. 1 shows the amino acid sequences of human histone H1 isoforms H1$^s$-1, H1$^s$-2, H1$^s$-3, H1$^s$-4, H1$^o$ and H1t.

FIG. 5 shows the reactivity of histone H1 derived peptides with the NANUC-1 and NANUC-2 antibodies.

FIG. 6 shows the growth conditions and media used to culture seven Mycobacterial strains: *M. tuberculosis*; *M. bovis*; *M. bovis* BCG; *M. smegmatis* 1-2c; *M. avium*; *M. avium paratuberculosis* and *M. avium paratuberculosis* "Linda" strain.

FIG. 8 shows the alignment of an N-terminal fragment of a *M. avium paratuberculosis* histone H1-like antigen (SEQ ID NO: 31; designated "N-term"); a predicted protein of 214 amino acids from the *M. tuberculosis* genome (SEQ ID NO: 27; designated "214"); and human histone H1 isoform H1.5 (SEQ ID NO: 32; designated "H1.5")

FIG. 10 shows the amino acid sequences of human histone H1.5 (SEQ ID NO: 32); a 214 amino acid *M. tuberculosis* histone H1-like antigen (SEQ ID NO: 27); a 323 amino acid outer membrane protein F precursor from *E. coli* (SEQ ID NO: 28); a 377 amino acid outer membrane protein F precursor from *E. coli* (SEQ ID NO: 29); and a 367 amino acid outer membrane protein c precursor from *E. coli* (SEQ ID NO: 30).

FIG. 11 shows the alignment of 19 amino acid sequence which is common to two *E. coli* porin antigens (SEQ ID NO: 33; designated "N-term"); the 323 amino acid outer membrane protein F precursor from *E. coli* (SEQ ID NO: 28; designated "323"); and human histone H1 isoform H1.5 (SEQ ID NO:32; designated "H1.5").

DETAILED DESCRIPTION OF THE INVENTION

Perinuclear anti-neutrophil cytoplasmic antibodies (pANCA) are present in the sera of most patients with ulcerative colitis (UC), and are a familial trait associated with disease susceptibility and disease-associated MHC haplotypes. Although sera from pANCA-positive ulcerative colitis patients are known to react with a component of neutrophils, the antigen responsible for the UC pANCA reactivity has long eluded identification. The present invention is directed to the exciting discovery that the pANCA autoantibody present in the sera of most patients with UC reacts with histone H1. The present invention further is directed to the discovery that UC pANCA also reacts with antigens of microbial origin. In particular, disclosed herein are a pANCA-reactive histone H1-like antigen, porin antigen and 100 kDa antigen selectively expressed in Bacteroides, each of which is a microbial antigen useful in the diagnosis, prevention and treatment of ulcerative colitis.

Figure 2:
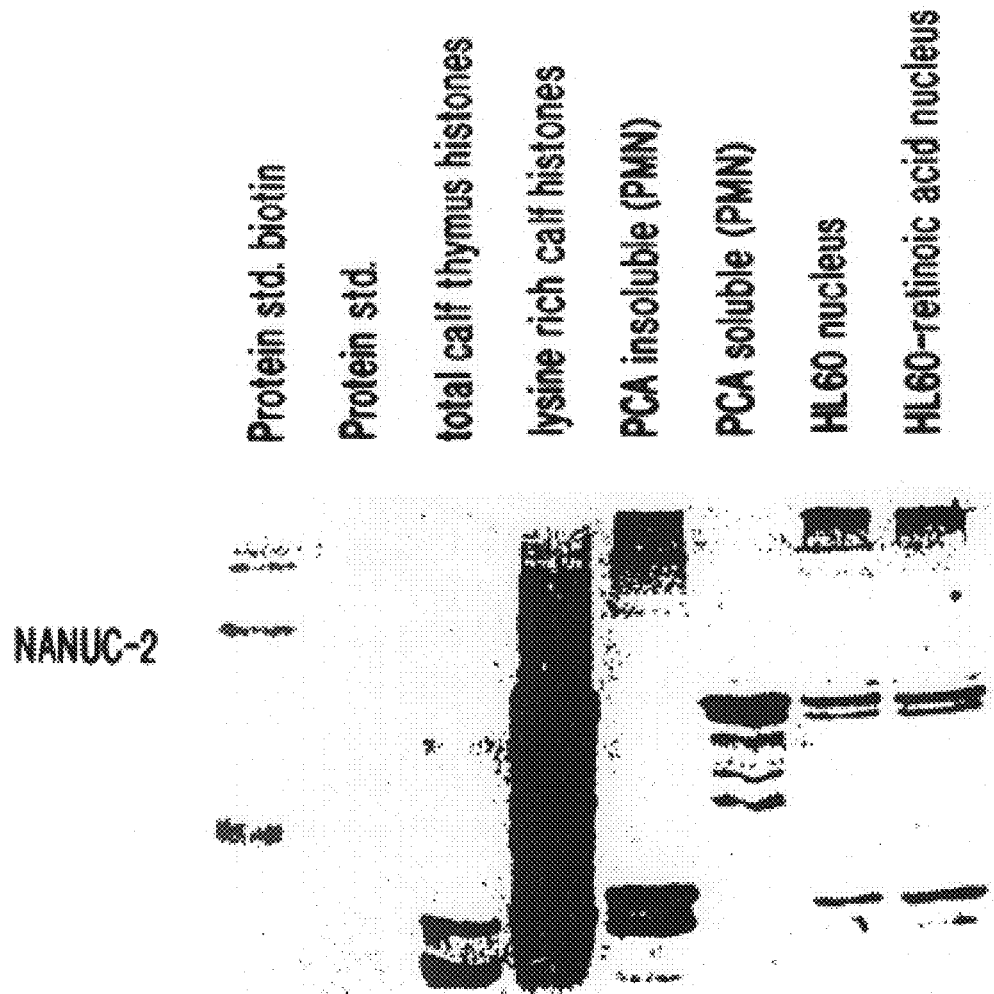
FIG. 2 shows Western analysis with a representative pANCA monoclonal, NANUC-2. Protein samples represent a HL60 cell nuclear fraction, purified calf thymus histones and histones purified from human neutrophils (PMN). The perchloric acid (PCA) insoluble PMN fraction contains the core histones, while the perchloric acid soluble fraction contains histone H1.
Figure 3A:
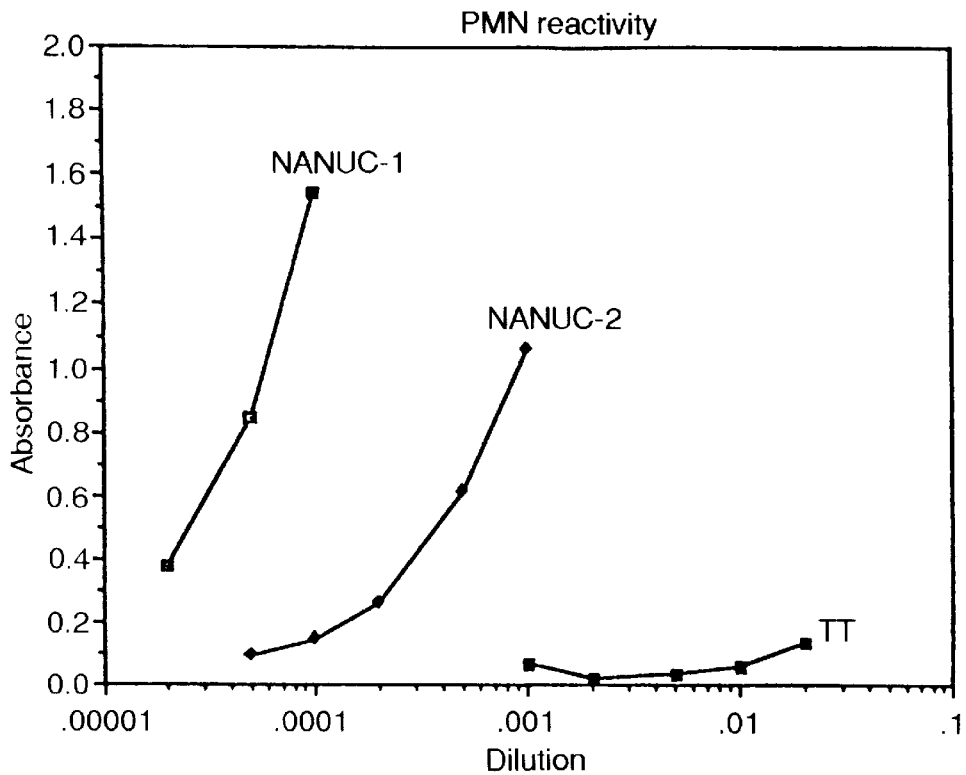
FIG. 3 shows enzyme-linked immunosorbent assay analysis of NANUC-1 and NANUC-2 with neutrophil (PMN), total calf thymus histones (histone), purified calf thymus histone H1 (H1) or tetanus toxoid antigen (TT).
Figure 3B:
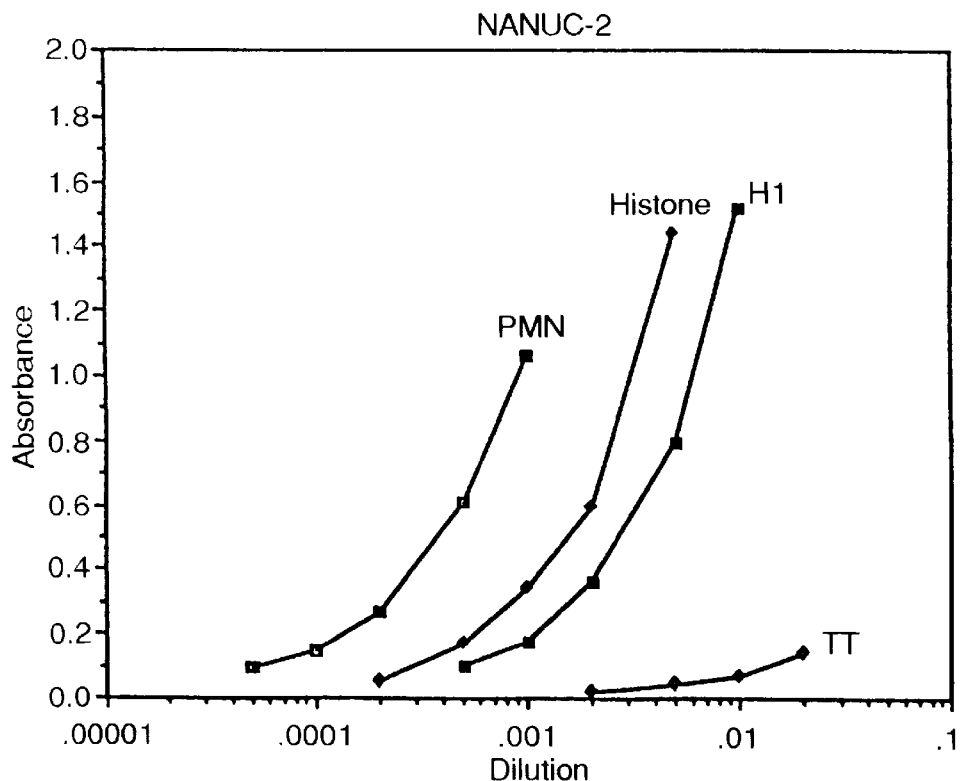
Figure 3C:
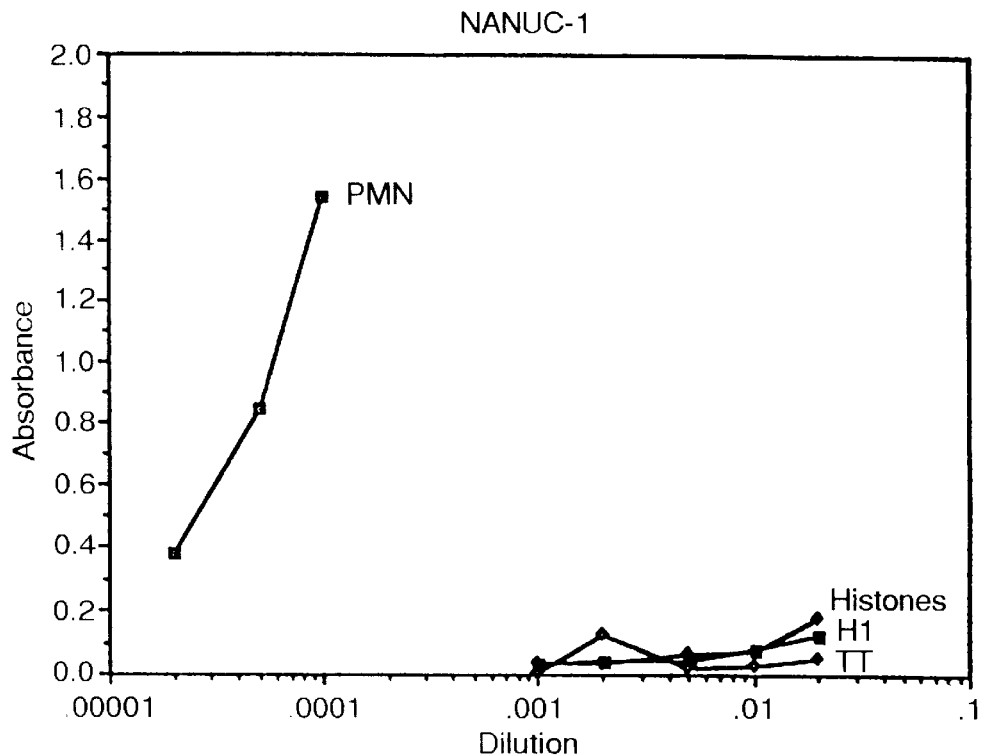
Figure 3D:
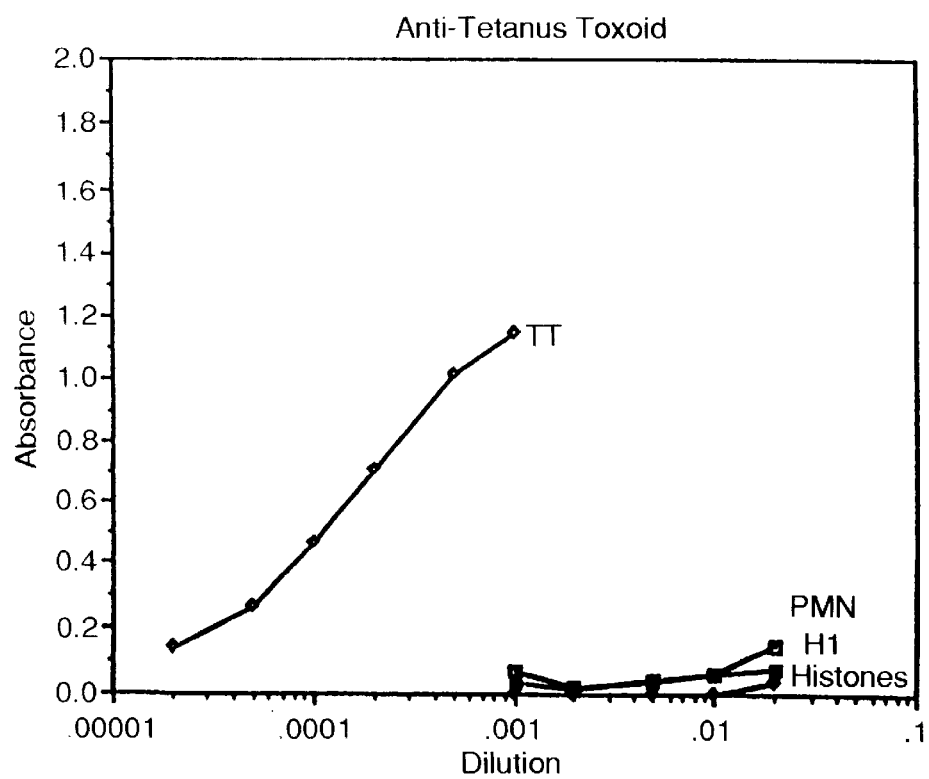

As disclosed herein, Western analysis demonstrates that a nuclear protein doublet of 32–33 kDa from neutrophils is specifically reactive with a representative UC pANCA monoclonal antibody, NANUC-2 (see FIG. 2). Purification and protein sequencing of the NANUC-2 reactive protein doublet identified the UC pANCA target antigen as histone H1. Specific binding of NANUC-2 to histone H1 was confirmed using purified human neutrophil histone H1 and purified calf thymus histone H1. Identification of histone H1 as a UC pANCA target antigen provides a valuable reagent for diagnosing the presence of pANCA in UC patients and for ameliorating the abnormal immune process involved in ulcerative colitis. Thus, the invention is directed to methods for diagnosing a pANCA-positive clinical subtype of UC and determining susceptibility to UC using histone H1. The invention also is directed to methods of treating UC by inducing tolerance in a pANCA-positive UC patient and preventing UC in a healthy individual by administering the recently identified UC pANCA target antigen, histone H1.

The present invention provides methods of diagnosing UC by obtaining a sample from a subject suspected of having inflammatory bowel disease; contacting the sample with human histone H1, or pANCA-reactive fragment thereof, under conditions 10 suitable to form a complex of human histone H1, or pANCA-reactive fragment thereof, and antibody to human histone H1; and detecting the presence or absence of the complex, where the presence of the complex indicates that the subject has ulcerative colitis. Human histone H1 useful in these methods can be, for example, histone H1 isoform $H1^s$-2 or a pANCA-reactive fragment thereof such as SEQ ID NO: 7, SEQ ID NO: 13, SEQ ID NO: 14 or SEQ ID NO: 20.

The present invention also provides methods of diagnosing a pANCA-positive clinical subtype of ulcerative colitis in a patient with UC. A pANCA-positive clinical subtype of UC can be diagnosed, for example, by obtaining a sample from a patient with UC; contacting the sample with human histone H1, or pANCA-reactive fragment thereof, under conditions suitable to form a complex of human histone H1, or pANCA-reactive fragment thereof, and antibody to human histone H1; and detecting the presence or absence of the complex, where the presence of the complex indicates that the patient has the pANCA-positive clinical subtype of UC. A pANCA-positive clinical subtype of UC also can be diagnosed by obtaining a sample from a patient with UC; contacting the sample with purified histone H1 isoform $H1^s$-2, or pANCA-reactive fragment thereof, under conditions suitable to form a complex of histone H1 isoform $H1^s$-2, or pANCA-reactive fragment thereof, and antibody to histone H1 isoform $H1^s$-2; and detecting the presence or absence of the complex, where the presence of the complex indicates that the patient has the pANCA-positive clinical subtype of UC.

The methods of the invention relate to diagnosing and treating UC, which is a disease of the large intestine characterized by chronic diarrhea with cramping abdominal pain, rectal bleeding, and loose discharges of blood, pus and mucus. The manifestations of this disease vary widely. A pattern of exacerbations and remissions typifies the clinical course of most UC patients (70%), although continuous symptoms without remission are present in some patients with UC. Local and systemic complications of UC include arthritis, eye inflammation such as uveitis, skin ulcers and liver disease. In addition, ulcerative colitis and especially long-standing, extensive disease is associated with an increased risk of colon carcinoma.

Several pathologic features characterize UC in distinction to other inflammatory bowel diseases. Ulcerative colitis is a diffuse disease that usually extends from the most distal part of the rectum for a variable distance proximally. The term left-sided colitis describes an inflammation that involves the distal portion of the colon, extending as far as the splenic flexure. Sparing of the rectum or involvement of the right side (proximal portion) of the colon alone is unusual in ulcerative colitis. Furthermore, the inflammatory process of UC is limited to the colon and does not involve, for example, the small intestine, stomach or esophagus. In addition, ulcerative colitis is distinguished by a superficial inflammation of the mucosa that generally spares the deeper layers of the bowel wall. Crypt abscesses, in which degenerate intestinal crypts are filled with neutrophils, also are typical of the pathology of ulcerative colitis (Rubin and Farber, *Pathology* (Second Edition) Philadelphia: J. B. Lippincott Company (1994), which is incorporated herein by reference).

As used herein, the term "ulcerative colitis" is synonymous with "UC" and means a disease having clinical features of left-sided colonic disease accompanied by a characteristic endoscopic or histopathologic feature of UC. Clinical features of left-sided colonic disease, as used herein, are rectal bleeding, urgency and tenesmus. The rectal bleeding may be accompanied by mucus discharge. Additional clinical features that may be present in UC include treatment with topical therapy and recommended or performed total or near-total colectomy.

A characteristic endoscopic feature of UC, which when present with clinical features of left-sided colonic disease indicates ulcerative colitis, is inflammation that is more severe distally than proximally or continuous inflammation. Additional typical endoscopic features that may be present in UC include inflammation extending proximally from the rectum or shallow ulcerations or the lack of deep ulcerations.

A characteristic histopathologic feature of UC, which when present with clinical features of left-sided colonic disease indicates ulcerative colitis, is homogeneous, continuous, predominantly superficial inflammation or a lack of "focality" within biopsy specimens. Additional typical histopathologic features that may be present in UC include the presence of crypt abscesses or a lack of granulomas. Characteristic clinical features of left-sided colonic disease and characteristic endoscopic and histopathologic features of ulcerative colitis are summarized in Table 1.

As used herein, the term "subject suspected of having inflammatory bowel disease" means any animal capable of having ulcerative colitis, including a human, non-human primate, rabbit, rat or mouse, especially a human, and having one or more symptoms of ulcerative colitis or Crohn's disease as described hereinabove.

As used herein, the term "patient with UC" means a patient having ulcerative colitis, as defined by the presence of clinical features of left-sided colonic disease accompanied by a characteristic endoscopic or histopathologic feature of UC as defined herein.

The pathogenesis of ulcerative colitis, although poorly understood, ultimately involves immune-mediated tissue damage. Ulcerative colitis is associated with various immunologic abnormalities, many of which can be secondary to inflammation. Similar to autoimmune disorders such as diabetes mellitus and multiple sclerosis, ulcerative colitis can represent a process of immune dysfunction directed against intrinsic intestinal mucosa cells. However, ulcerative colitis occurs in a mucosal site interfacing with the intestinal lumen. Thus, a primary immune target also can be an extrinsic agent such as a chronic microbial colonist. In this case, the mucosal injury characteristic of UC is a consequence of inflammatory bystander damage to resident parenchymal cells.

TABLE 1

| | |
|---|---|
| A. Clinical features of left-sided colonic disease | 1. Rectal bleeding possibly accompanied by mucus discharge<br>2. Urgency<br>3. Tenesmus<br>4. Treatment with topical therapy<br>5. Recommended or performed total or near-total colectomy |
| B. Endoscopic features of UC | 6. Inflammation that is more severe distally than proximally<br>7. Continuous inflammation<br>8. Inflammation extending proximally from the rectum<br>9. Shallow ulcerations or lack of deep ulcerations |
| C. Histopathologic features of UC | 10. Homogeneous, continuous, predominantly superficial inflammation<br>11. Lack of "focality" within biopsy specimens<br>12. Crypt abscesses<br>13. Lack of granulomas |

Host genetic factors can confer susceptibility or resistance to tissue damage elicited by a chronic local immune response. For example, IBD is associated with polymorphisms in MHC class II, ICAM-1 and TNF-α loci (Yang et al., *J. Clin. Invest.* 92:1080–1084 (1993)), and animal and clinical studies directly implicate TNF levels in disease. In the case of autoimmune diseases where the primary target is a self-antigen, host genetic factors can play a role in disease by controlling, for example, T-cell clonal abundance, peptide antigen presentation, and levels of cytokines modulating different effector responses. Host genetic diversity also can affect variable susceptibility to microbial organisms. Thus, pathogenesis of ulcerative colitis can result from a primary abnormality of the immune system, or from an initial injury by an infectious agent that is perpetuated through immune-mediated or other processes.

Certain immune-mediated disorders, including systemic lupus erythematosis, primary biliary cirrhosis and autoimmune hepatitis, are closely associated with distinctive patterns of autoantibody production. In the case of ulcerative colitis, anti-neutrophil cytoplasmic antibodies that produce a perinuclear staining pattern (pANCA) are elevated in 68–80% of UC patients and less frequently in other disorders of the colon. Serum titers of ANCA are elevated regardless of clinical status and, thus, do not reflect disease activity. High levels of serum ANCA also persist in patients five years post-colectomy. Although pANCA is found only very rarely in healthy adults and children, healthy relatives of UC patients have an increased frequency of pANCA, indicating that pANCA may be an immunogenetic susceptibility marker.

Serum antibodies to cytoplasmic components of a neutrophil (ANCA) can be detected, for example, using indirect immunofluorescence microscopy of alcohol-fixed neutrophils. ANCA activity has been divided into two broad categories: cytoplasmic neutrophil staining (cANCA) and perinuclear to nuclear staining or cytoplasmic staining with perinuclear highlighting (pANCA). As used herein, the term "perinuclear anti-neutrophil cytoplasmic antibody" is synonymous with "pANCA" and means an antibody that reacts specifically with a neutrophil to give perinuclear to nuclear staining or cytoplasmic staining with perinuclear highlighting.

The term "clinical subtype of UC," as used herein, means a subgroup of patients having ulcerative colitis whose features of disease are more similar to each other than to other patients with ulcerative colitis. The term "pANCA-positive clinical subtype of UC" means that subgroup of UC patients having pANCA.

Serum anti-neutrophil cytoplasmic antibodies previously have been used to characterize clinically distinct subsets of UC patients. For example, the presence of pANCA has been associated with treatment-resistant left-sided ulcerative colitis; aggressive UC (Vecchi et al., *Digestion* 55:34–39 (1994)); the requirement for surgery early in the course of UC (Boerr et al., *Gastroenterol.* 108: A785 (1995)) or development of pouchitis following ileal pouch-anal anastomosis for UC (Sandborn et al., *Gastroenterol.* 104: A774 (1993); Patel et al., *Br. J. Surg.* 81:724–726 (1994); Vecchi et al., *Lancet* 344:886–887 (1994); Sandborn et al., *Am. J. Gastroenterol.* 90:740–747 (1995)). Thus, the ability to identify a pANCA-positive clinical subtype of UC can be useful in predicting, for example, treatment-resistant UC; the progression of UC; the need for early surgery or the development of pouchitis.

The present invention is directed to the surprising discovery that an antigen that reacts with pANCA of ulcerative colitis is histone H1. Thus, the UC pANCA target antigen is a member of the histone family, which are highly-conserved proteins characterized by basic residues that contact the negatively charged phosphate groups in DNA and organize the DNA of eukaryotes into chromatin. Histones H2A, H2B, H3 and H4 are the core histones that make up nucleosomes, while histone H1, which is associated with nucleosomes at a 1 to 1 ratio, is required for higher order chromatin structure.

Histone H1 has a conserved central globular domain with extended, flexible N- and C-terminal domains. Sites of reversible chemical modification, such as phosphorylation and acetylation, occur in these extended N- and C-terminal regions and can regulate histone-DNA interactions (Bradbury et al., *Bioessays* 14: 9–16 (1992)). The histone H1 family has multiple isoforms including $H1^s$-1, $H1^s$-2, $H1^s$-3 and $H1^s$-4, which are present in all normal somatic cells; the highly variable $H1°$ isoform, which is associated with differentiated cell types; and the testis-specific isoform H1t (Parseghian et al., *Protein Sci.* 3:575–587 (1994), which is incorporated herein by reference). That functional differences can be associated with alternative histone H1 isoforms is supported by differences among the isoforms in the time of protein synthesis; turnover rate; amount and pattern of phosphorylation and ability to condense DNA in vitro.

As used herein, the term "histone H1" means one or more proteins having at least about 80% amino acid identity with at least one amino acid sequence of human histone H1 isoform $H1^s$-1 (SEQ ID NO: 1); $H1^s$-2 (SEQ ID NO: 2); $H1^s$-3 (SEQ ID NO: 3); $H1^s$-4 (SEQ ID NO: 4); $H1°$ (SEQ ID NO: 5); H1t (SEQ ID NO: 6). Thus, the term histone H1 encompasses, for example, one or more of the human histone H1 isoforms having an amino acid sequence shown in FIG. 1.

The term histone H1 also encompasses one or more non-human histone H1 isoforms having at least about 80% amino acid identity with at least one of the human histone H1 isoforms having an amino acid sequence shown in FIG. 1. For example, the term histone H1 encompasses, for example, a mouse or bovine $H1^s$-1 isoform having an amino acid sequence described in Parseghian et al., supra, 1994, or a rabbit or bovine $H1^s$-2 isoform having an amino acid sequence described in Parseghian et al., supra, 1994. Similarly, the term histone H1 encompasses, for example, a rabbit or rat $H1^s$-3 isoform having an amino acid sequence described in Parseghian et al., supra, 1994, or a mouse, rat, rabbit or bovine H1$^s$-4 isoform having an amino acid sequence described in Parseghian et al., supra, 1994. As disclosed herein, histone H1 useful in the invention can be obtained from a variety of species. For example, histone H1 that forms a complex with a representative UC monoclonal antibody (NANUC-2) and, thus, can form a complex with pANCA, can be purified from human neutrophil or calf thymus as described in Example I.

As used herein, the term "human histone H1" means one or more proteins having at least one amino acid sequence of human histone H1 isoform H1$^s$-1 (SEQ ID NO: 1); H1$^s$-2 (SEQ ID NO: 2); H1$^s$-3 (SEQ ID NO: 3); H1$^s$-4 (SEQ ID NO: 4); H1$^o$ (SEQ ID NO: 5) or H1t (SEQ ID NO: 6).

As used herein, the term "histone H1 isoform H1$^s$-3" is synonymous with "H1$^s$-3" and means a protein having at least about 80% amino acid identity with the amino acid sequence of human histone isoform H1$^s$-3 (SEQ ID NO: 3) shown in FIG. 1. For example, the term H1$^s$-3 encompasses human histone H1 isoform H1$^s$-3 having the amino acid sequence (SEQ ID NO: 3) shown in FIG. 1. The term H1$^s$-3 also encompasses a non-human H1-3 protein having at least about 80% amino acid identity with the amino acid sequence shown as SEQ ID NO: 3, such as a rabbit or rat H1$^s$-3 isoform having an amino acid sequence described in Parseghian et al., supra, 1994.

As used herein, the term "histone H1 isoform H1$^s$-2" is synonymous with "H1$^s$-2" and means a protein having at least about 80% amino acid identity with the amino acid sequence of human histone isoform H1$^s$-2 (SEQ ID NO: 2) shown in FIG. 1. For example, the term H1$^s$-2 encompasses human histone H1 isoform H1$^s$-2 having the amino acid sequence (SEQ ID NO: 2) shown in FIG. 1. The term H1$^s$-2 also encompasses a non-human H1$^s$-2 protein having at least about 80% amino acid identity with the amino acid sequence shown as SEQ ID NO: 2, such as a rat or bovine H1$^s$-2 isoform having an amino acid sequence described in Parseghian et al., supra, 1994.

Figure 7:
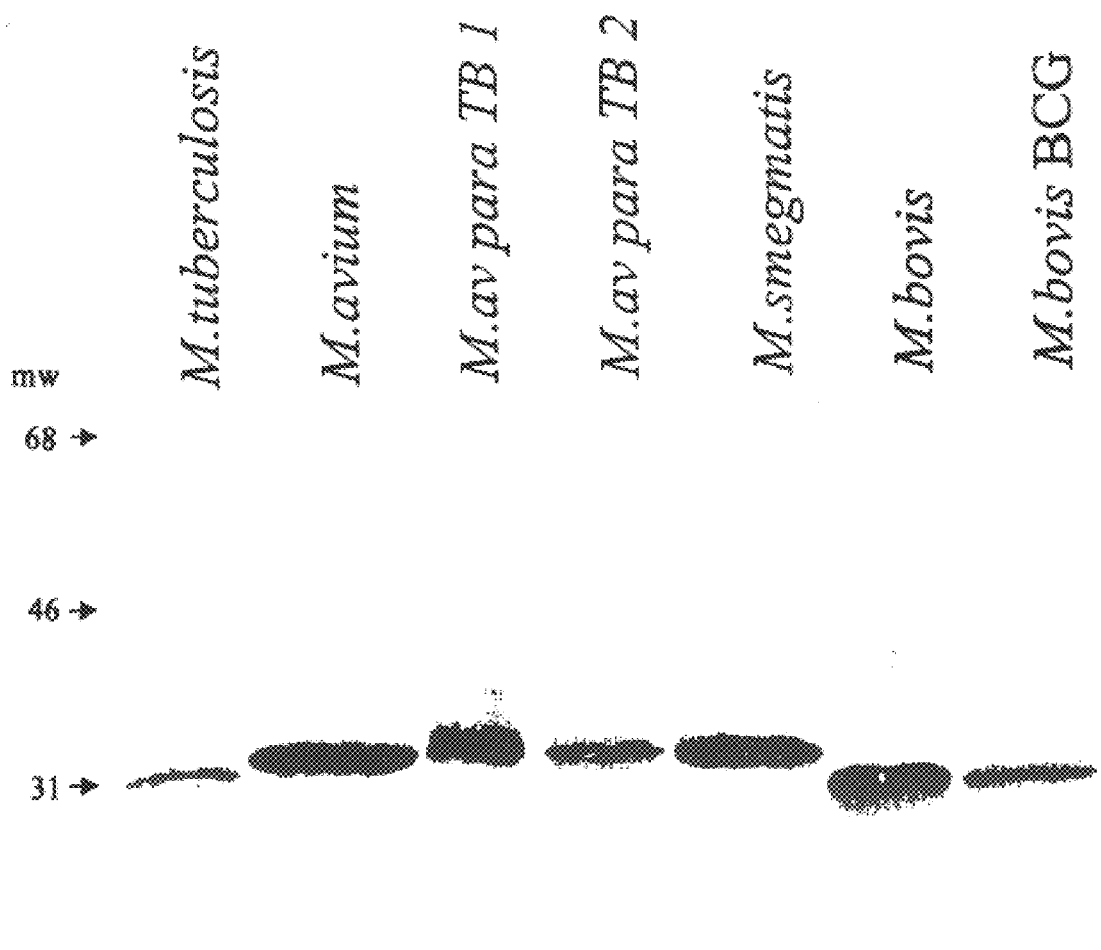
FIG. 7 shows Western analysis of seven Mycobacterial strains with the NANUC-2 antibody. Each of the seven strains express a pANCA-reactive protein of 30–32 kDa.

As further disclosed herein, Western analysis demonstrates that an antigen of 30–32 kDa present in various species of Mycobacteria is specifically reactive with NANUC-2, a representative UC pANCA monoclonal antibody (see FIG. 7). Isolation and amino-terminal sequencing of the 30–32 kDa protein from *M. avium paratuberculosis* revealed that the amino-terminal sequence was nearly identical to the amino-terminal sequence of a predicted *M. tuberculosis* protein of 214 amino acids (SEQ ID NO: 27). This *M. tuberculosis* protein shares 48% sequence similarity with human histone H1 isoform H1.5 (SEQ ID NO: 32) (see FIG. 8), indicating that the 214 amino acid *M. tuberculosis* protein is a histone H1-like antigen. Immunoreactivity with NANUC-2 confirmed that the 214 amino acid *M. tuberculosis* protein (SEQ ID NO: 27) is a UC pANCA antigen.

Identification of a pANCA-reactive Mycobacterial histone H1-like antigen implicates Mycobacteria in the pathogenesis of UC and provides a valuable reagent for diagnosing or ameliorating UC. Based on this finding, the present invention provides methods for diagnosing UC or a pANCA-positive clinical subtype of UC as well as methods of determining susceptibility to UC. The present invention also provides methods of treating UC and methods of preventing UC in a healthy individual by administering the recently identified UC pANCA target antigen, a histone H1-like antigen.

In particular, the present invention provides methods of diagnosing UC by obtaining a sample from a subject suspected of having inflammatory bowel disease; contacting the sample with a histone H1-like antigen, or pANCA-reactive fragment thereof, under conditions suitable to form a complex of the histone H1-like antigen, or pANCA-reactive fragment thereof, and antibody to the histone H1-like antigen; and detecting the presence or absence of the complex, where the presence of the complex indicates that the subject has ulcerative colitis. A histone H1-like antigen useful in these methods can be, for example, a protein immunoreactive with NANUC-2 and having at least 65% amino acid identity with SEQ ID NO: 27.

The present invention also provides methods of diagnosing a pANCA-positive clinical subtype of ulcerative colitis in a patient with UC. A pANCA-positive clinical subtype of UC can be diagnosed, for example, by obtaining a sample from a patient with UC; contacting the sample with a histone H1-like antigen, or pANCA-reactive fragment thereof, under conditions suitable to form a complex of the histone H1-like antigen, or pANCA-reactive fragment thereof, and antibody to histone H1-like antigen; and detecting the presence or absence of the complex, where the presence of the complex indicates that the patient has the pANCA-positive clinical subtype of UC.

As used herein, the term "histone H1-like antigen" means a pANCA-reactive protein having linear or conformational homology to histone H1. A histone H1-like antigen generally is characterized as having at least about 48% amino acid similarity with one or more of the following human histone H1 isoforms: Hs-1 (SEQ ID NO: 1); H1$^s$-2 (SEQ ID NO: 2); H1$^s$-3 (SEQ ID NO: 3); H1$^s$-4 (SEQ ID NO: 4); H1$^o$ (SEQ ID NO: 5); or H1t (SEQ ID NO: 6).

The term "histone H1-like antigen" encompasses, for example, a microbial histone H1-like antigen, which is a histone H1-like antigen of microbial origin having a molecular weight of about 30–32 kDa on SDS-PAGE analysis. An example of a microbial histone H1-like antigen is a 30–32 kDa protein which is-immunoreactive with NANUC-2 and is isolated from a Mycobacteria such as *M. tuberculosis; M. bovis,* and *M. bovis* BCG; *M. smegmatis* 1–2c; *M. avium; M. avium paratuberculosis* and *M. avium paratuberculosis* "Linda" strain (see FIG. 7). A microbial histone H1-like antigen can be, for example, the *M. tuberculosis* histone H1-like protein (SEQ ID NO: 27).

The term histone H1-like antigen encompasses a protein that has at least 65% amino acid identity with the 214 amino acid *M. turberculosis* histone H1-like antigen (SEQ ID NO: 27). In particular, a histone H1-like antigen can have an amino acid sequence having, for example, at least 70%, 80%, 85%, 90% or 95% amino acid identity with SEQ ID NO: 27.

A histone H1-like antigen can be isolated from a variety of eukaryotic and prokaryotic organisms, including bacteria such as Mycobacteria and others. A histone H1-like antigen can be isolated from a variety of species of Mycobacteria, including *Mycobacterium tuberculosis, Mycobacterium bovis, Mycobacterium smegmatis* 1–2c, *Mycobacterium avium* and *Mycobacterium avium paratuberculosis.* Histone H1-like antigens isolated from a variety of Mycobacterial species are disclosed in Example V.

The present invention also relates to a UC pANCA porin antigen expressed by enteric bacteria of UC patients. As disclosed in Example VI, Western analysis demonstrates that a 35 kDa protein isolated from colonic *E. coli* of UC patients is specifically reactive with the UC pANCA monoclonal antibody NANUC-2 (see FIG. 9). The larger and smaller of two pANCA-reactive *E. coli* proteins were isolated and each sequenced from the N-terminus, revealing identical N-terminal sequence (SEQ ID NO: 33). This amino-terminal sequence indicated that the two pANCA-reactive *E. coli* proteins were related to the outer membrane proteins F and C (OmpF and OmpC; see FIG. 10). As shown in FIG. 11, the porin antigen of the invention lacks detectable linear sequence homology with histone H1 but can have conformational sequence homology with one or more pANCA-reactive epitopes of histone H1. These results indicate that microbial antigens lacking detectable linear sequence homology to histone H1 can be expressed by enteric colonic bacteria in UC patients and can play a role in the immune dysregulation in UC.

Isolation of the porin antigen disclosed herein provides a novel UC pANCA target antigen for diagnosing and treating ulcerative colitis. Based on this discovery, the invention provides methods for diagnosing UC or a pANCA-positive clinical subtype of UC and methods of determining susceptibility to UC using a porin antigen. The invention further provides methods of treating UC by inducing tolerance in a pANCA-positive UC patient and methods of preventing UC in a healthy individual by administering a porin antigen.

In particular, the present invention provides a method of diagnosing UC by obtaining a sample from a subject suspected of having inflammatory bowel disease; contacting the sample with a porin antigen, or pANCA-reactive fragment thereof, under conditions suitable to form a complex of the porin antigen, or pANCA-reactive fragment thereof, and antibody to the porin antigen; and detecting the presence or absence of the complex, where the presence of the complex indicates that the subject has ulcerative colitis. A porin antigen useful in these methods can be, for example, a protein immunoreactive with NANUC-2 and having an amino acid sequence having at least 65% amino acid identity with SEQ ID NO: 28, SEQ ID NO: 29 or SEQ ID NO: 30.

The present invention also provides methods of diagnosing a pANCA-positive clinical subtype of ulcerative colitis in a patient with UC. A pANCA-positive clinical subtype of UC can be diagnosed, for example, by obtaining a sample from a patient with UC; contacting the sample with a porin antigen, or pANCA-reactive fragment thereof, under conditions suitable to form a complex of the porin antigen, or pANCA-reactive fragment thereof, and antibody to porin, antigen; and detecting the presence or absence of the complex, where the presence of the complex indicates that the patient has the pANCA-positive clinical subtype of UC.

The porin antigens disclosed herein belong to a class of transmembrane proteins that are found in the outer membranes of bacteria, including gram-negative, enteric bacteria such as *E. coli*. The porins in the outer membrane of an *E. coli* cell provide channels for passage of disaccharides, phosphate and similar molecules. Porins can be trimers of identical subunits arranged to form a barrel-shaped structure with a pore at the center (Lodish et al., *Molecular Cell Biology*, Chapter 14 (1995), which is incorporated herein by reference).

Two major porin proteins found in the outer membranes of bacteria such as *E. coli* are outer-membrane protein F ("OmpF") and outer-membrane protein C ("OmpC"). These two porins are similar in structure and function, assembling as trimers in the outer membrane to form aqueous channels that allow the passive diffusion of small, hydrophilic molecules across the hydrophobic barrier. The diameters of the OmpF and OmpC pores differ with the pore of OmpF being 1.2 nm while the diameter of the OmpC pore is 1.1 nm. This difference results in a faster rate of diffusion through the OmpF pores than through the OmpC pores.

Porin expression can be influenced by environmental conditions, including osmolarity, temperature, growth phase and toxin concentration. For example, in the intestine, where both nutrient and toxic molecule concentrations are relatively high, OmpC, with a smaller pore diameter, is the predominant porin (Pratt et al., *Mol. Micro.*, 20:911–917 (1996), which is incorporated herein by reference).

As used herein, the term "porin antigen" means a pANCA-reactive protein that has linear or conformational homology to OmpF, OmpC or another *E. coli* porin. A porin antigen generally is a protein that, in nature, forms a trimeric structure in the outer membrane of bacteria that allows the passage of small molecules, or a precursor of such a protein. A porin antigen can be derived from a gram-negative bacterium, such as *E. coli*, and can be, for example, OmpF or OmpC, or a homolog thereof.

The term "porin antigen," as used herein, encompasses a protein that has at least 65% amino acid identity with one or more of the following proteins: SEQ ID NO: 28, SEQ ID NO: 29 or SEQ ID NO: 30. A porin antigen can have, for example, at least 70%, 80%, 85%, 90% or 95% amino acid identity with SEQ ID NO: 28, SEQ ID NO: 29 or SEQ ID NO: 30.

The present invention also relates to a novel UC pANCA target antigen derived from Bacteroides. Bacteroides is a genus of gram-negative, anaerobic, nonspore-forming, rod-shaped bacteria. They are normal inhabitants of the intestinal tract, and may constitute the predominant bacteria of the normal human colon. Some species of Bacteroides are known to be pathogenic, causing serious abscesses and bacteriomas.

Figure 9A:
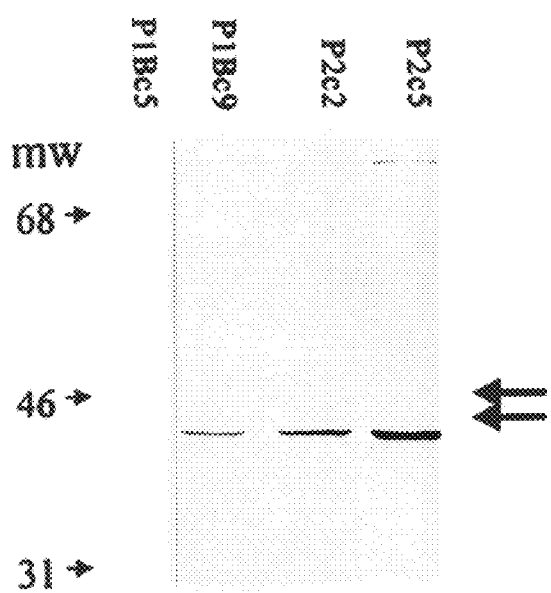
FIG. 9 shows Western analysis of UC patient colonic bacterial isolates with the NANUC-2 antibody. A. Whole cell extracts of four *E. coli* isolates (designated P1Bc5, P1Bc9, P2c2 and P2c5). B. Whole cell extracts from *E. coli* isolate P2Lc2 and two *Bacteroides cecae* isolates (designated P2Lc3 and P2Lc5).
Figure 9B:
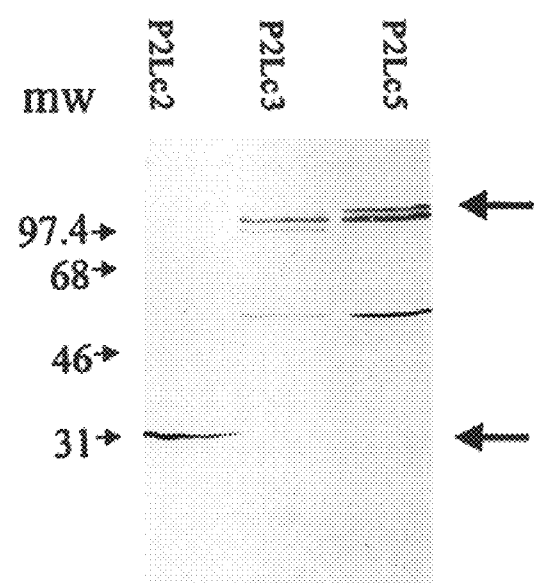

As disclosed herein, an antigen of about 100 kDa isolated from extracts of *Bacteroides cecae* is specifically reactive with NANUC-2 (see FIG. 9B). This pANCA-reactive antigen is selectively expressed in Bacteroides and is not expressed in all bacteria, for example, in *E. coli* (see FIG. 9; compare lanes 2 and 3 of panel B with other lanes). Identification of a Bacteroides antigen as a UC pANCA target antigen provides an additional valuable reagent for diagnosing the presence of pANCA in UC patients and for treating the disease. The Bacteroides antigen disclosed herein can be used alone for diagnosis or treatment of UC, or can be used in combination with one or more other UC pANCA target antigens such as those disclosed herein.

Thus, the present invention provides methods of diagnosing UC by obtaining a sample from a subject suspected of having inflammatory bowel disease; contacting the sample with a Bacteroides antigen, or pANCA-reactive fragment thereof, under conditions suitable to form a complex of the Bacteroides antigen, or pANCA-reactive fragment thereof, and antibody to the Bacteroides antigen; and detecting the presence or absence of the complex, where the presence of the complex indicates that the subject has ulcerative colitis. A Bacteroides antigen useful in these methods can be, for example, a *Bacteroides cecae* protein immunoreactive with NANUC-2 and having a molecular weight of about 100 kDa by SDS-PAGE electrophoresis.

The present invention also provides methods of diagnosing a pANCA-positive clinical subtype of ulcerative colitis in a patient with UC. A pANCA-positive clinical subtype of UC can be diagnosed, for example, by obtaining a sample from a patient with UC; contacting the sample with a Bacteroides antigen, or pANCA-reactive fragment thereof, under conditions suitable to form a complex of the Bacteroides antigen, or pANCA-reactive fragment thereof, and antibody to Bacteroides antigen; and detecting the presence or absence of the complex, where the presence of the complex indicates that the patient has the pANCA-positive clinical subtype of UC.

As used herein, the term "Bacteroides antigen" means a microbial pANCA-reactive protein of about 100 kDa that is selectively expressed, at least in part, in Bacteroides. A Bacteroides antigen can be a *Bacteroides cecae* antigen and can be isolated as described in Example VI.

A sample useful in the methods of the invention can be obtained from any biological fluid having pANCA such as, for example, whole blood, plasma or other bodily fluid or tissue having pANCA, preferably serum. As used herein, the term "patient" means any animal capable of producing pANCA, including, for example, a human, non-human primate, rabbit, rat or mouse. A sample to be assayed according to the methods of the invention can be obtained from any such patient.

As used herein, the term "complex" is synonymous with "immune complex" and means an aggregate of two or more molecules that results from specific binding between an antigen, such as a protein or peptide, and an antibody. For example, a complex can be formed by specific binding of histone H1 to an antibody against histone H1.

As used herein, the term "antibody" means a population of immunoglobulin molecules, which can be polyclonal or monoclonal and of any isotype. As used herein, the term antibody encompasses an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or $F(ab')_2$ is included within the meaning of the term antibody.

As used herein, the term "secondary antibody" means an antibody or combination of antibodies, which binds pANCA of UC. Preferably, a secondary antibody does not compete with histone H1 or another antigen of the invention for binding to pANCA. A secondary antibody can be an anti-pANCA antibody that binds any epitope of pANCA. A particularly useful secondary antibody is an anti-IgG antibody having specificity for the class determining portion of pANCA. A useful secondary antibody is specific for the species of the ANCA to be detected. For example, if human serum is the sample to be assayed, mouse anti-human IgG can be a useful secondary antibody. A combination of different antibodies, which can be useful in the methods of the invention, also is encompassed within the meaning of the term secondary antibody, provided that at least one antibody of the combination binds pANCA of UC.

As used herein, the term "class determining portion," when used in reference to a secondary antibody, means the heavy chain constant-region sequence of an antibody that determines the isotype, such as IgA, IgD, IgE, IgG or IgM. Thus, a secondary antibody that has specificity for the class determining portion of an IgG molecule, for example, binds IgG in preference to other antibody isotypes.

A secondary antibody useful in the invention can be obtained commercially or by techniques well known in the art. Such an antibody can be a polyclonal or, preferably, monoclonal antibody that binds pANCA. For example, IgG reactive polyclonal antibodies can be prepared using IgG or Fc fragments of IgG as an immunogen to stimulate the production of antibodies in the antisera of an animal such as a rabbit, goat, sheep or rodent, as described in Harlow and Lane, *Antibodies: A Laboratory Manual* New York: Cold Spring Harbor Laboratory (1988), which is incorporated herein by reference.

A monoclonal antibody also is useful in the practice of the invention. As used herein, a monoclonal antibody refers to a population of antibody molecules that contain only one species of idiotope capable of binding a particular antigen epitope. Methods of producing a monoclonal antibody are well known (see, for example, Harlow and Lane, supra, 1988). An immunogen useful in generating a monoclonal antibody that binds pANCA can be, for example, human IgG or a Fc fragment of human IgG, pANCA or a Fab fragment of pANCA. A hybridoma that produces a useful monoclonal antibody can be identified by screening hybridoma supernatants for the presence of antibodies that bind pANCA (Harlow, supra, 1988). For example, hybridoma supernatants can be screened using neutrophil and pANCA-positive sera in a radioimmunoassay or enzyme-linked immunosorbent assay. n addition, a monoclonal antibody useful in the invention tan be obtained from a number of commercial sources.

The term "detectable secondary antibody" means a secondary antibody, as defined above, that can be detected or measured by analytical methods. Thus, the term secondary antibody includes an antibody labeled directly or indirectly with a detectable marker that can be detected or measured and used in a convenient assay such as an enzyme-linked immunosorbent assay, radioimmunoassay, radial immunodiffusion assay or Western blotting assay, for example. A secondary antibody can be labeled, for example, with an enzyme, radioisotope, fluorochrome or chemiluminescent marker. In addition, a secondary antibody can be rendered detectable using a biotin-avidin linkage such that a detectable marker is associated with the secondary antibody. Labeling of the secondary antibody, however, should not impair binding of the secondary antibody to pANCA of UC. If desired, a multiple antibody system can be used as the secondary antibody as discussed above. In such a system, at least one of the antibodies is capable of binding pANCA of UC and at least one of the antibodies can be readily detected or measured by analytical methods.

A secondary antibody can be rendered detectable by labeling with an enzyme such as horseradish peroxidase (HRP), alkaline phosphatase (AP), β-galactosidase or urease, for example. A horseradish-peroxidase detection system can be used, for example, with the chromogenic substrate tetramethylbenzidine (TMB), which yields a soluble product in the presence of hydrogen peroxide that is detectable by measuring absorbance at 450 nm. An alkaline phosphatase detection system can be used with the chromogenic substrate p-nitrophenyl phosphate, for example, which yields a soluble product readily detectable by measuring absorbance at 405 nm. Similarly, a β-galactosidase detection system can be used with the chromogenic substrate o-nitrophenyl-β-D-galactopyranoside (ONPG), which yields a soluble product detectable by measuring absorbance at 410 nm, or a urease detection system can be used with a substrate such as urea-bromocresol purple (Sigma Immunochemicals, St. Louis, Mo.). A secondary antibody can be linked to an enzyme by methods well known in the art (Harlow and Lane, supra, 1988) or can be obtained from a number of commercial sources. For example, goat F(ab')2 anti-human IgG-alkaline phosphatase is a useful detectable secondary antibody that can be purchased from Jackson Immuno-Research (West Grove, Pa.).

A secondary antibody also can be rendered detectable by labeling with a fluorochrome. Such a fluorochrome emits light of ultraviolet or visible wavelength after excitation by light or another energy source. DAPI, fluorescein, Hoechst 33258, R-phycocyanin, B-phycoerythrin, R-phycoerythrin, rhodamine, Texas red or lissamine, for example, is a fluorochrome that can be linked to a secondary antibody and used to detect the presence or absence of a complex. A particularly useful fluorochrome is fluorescein or rhodamine. Methods of conjugating and using these and other suitable fluorochromes are described, for example, in Van Vunakis and Langone, *Methods in Enzymoloay,* Volume 74, Part C (1991), which is incorporated herein by reference. A secondary antibody linked to a fluorochrome also can be obtained from commercial sources. For example, goat F(ab')2 anti-human IgG-FITC is available from Tago Immunologicals (Burlingame, Calif.).

A pANCA titer also can be determined using a secondary antibody labeled with a chemiluminescent marker. Such a chemiluminescent secondary antibody is convenient for sensitive, non-radioactive detection of pANCA and can be obtained commercially from various sources such as Amersham Lifesciences, Inc. (Arlington Heights, Ill.).

A secondary antibody further can be rendered detectable by labeling with a radioisotope. An iodine-125 labeled secondary antibody is a particularly useful detectable secondary antibody (see, for example, Harlow and Lane, supra, 1988).

A signal from a detectable secondary antibody can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis of the amount of ANCA can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

The assays of the present invention can be forward, reverse or simultaneous as described in U.S. Pat. No. 4,376,110, issued Mar. 8, 1983, to David et al., which is incorporated herein by reference. In the forward assay, each reagent is sequentially contacted with histone H1 or another antigen of the invention. If desired, separation of bound from unbound reagent can be performed before the addition of the next reagent. In a reverse assay, all reagents are pre-mixed prior to contacting histone H1 or another antigen of the invention. A modified reverse assay is described in U.S. Pat. No. 4,778,751 issued Oct. 18, 1988, to El Shami et al., which is incorporated herein by reference. In a simultaneous assay, all reagents are separately but contemporaneously contacted with histone H1 or another antigen of the invention. As used herein, reagent means any component useful to perform the assays of the present invention, for example, the sample, histone H1 or another antigen of the invention, detectable secondary antibody, washing buffer or other solutions.

Separation steps for the various assay formats described herein, including the removal of unbound secondary antibody from the complex, can be performed by methods known in the art (Harlow and Lane, supra, 1988). For example, washing with a suitable buffer can be followed by filtration, aspiration or magnetic separation. If histone H1, another antigen of the invention, or a pANCA-reactive fragment thereof is immobilized on a particulate support, such as on microparticles, the particulate material can be centrifuged, if desired, followed by removal of wash liquid. If histone H1, another antigen of the invention, or a pANCA-reactive fragment thereof is immobilized on a membrane, filter or well, a vacuum or liquid absorbing apparatus can by applied to the opposite side of the membrane, filter or well to draw the wash liquid away from the complex.

The invention also provides methods of determining susceptibility to UC in an individual by obtaining a sample from the individual; contacting the sample with human histone H1, or pANCA-reactive fragment thereof, under conditions suitable to form a complex of human histone H1, or pANCA-reactive fragment thereof, and antibody to human histone H1; and detecting the presence or absence of the complex, where the presence of the complex indicates that the individual has increased susceptibility to UC. Susceptibility to UC in an individual also can be determined by obtaining a sample from the individual; contacting the sample with purified histone H1 isoform $H1^s$-2, or pANCA-reactive fragment thereof, under conditions suitable to form a complex of purified histone H1 isoform H1-2, or pANCA-reactive fragment thereof, and antibody to histone H1 isoform $H1^s$-2; and detecting the presence or absence of the complex, where the presence of the complex indicates that the individual has increased susceptibility to UC.

The term "individual," as used herein, means any animal capable of producing pANCA, including a human, non-human primate, rabbit, rat or mouse, provided that the animal does not have ulcerative colitis as defined by the clinical, endoscopic and histopathologic parameters disclosed herein. A sample to be assayed according to the methods of the invention can be obtained from any such individual.

As used herein, the term "susceptibility to UC," when used in reference to an individual, means an inability to resist ulcerative colitis disease-causing factors. As used herein, the term "increased susceptibility to UC," as indicated by the presence of a complex of histone H1 and antibody to histone H1, means an increased inability to resist ulcerative colitis disease-causing factors, as compared with an individual from whom a sample is obtained that does not form a complex when contacted with histone H1, or pANCA-reactive fragment thereof. Similarly, increased susceptibility to UC that is indicated by the presence of a complex of a histone H1-like antigen, a porin antigen or a Bacteroides antigen, and antibody to one of these antigens, means an increased inability to resist ulcerative colitis disease-causing factors, as compared with an individual from whom a sample is obtained that does not form such a complex. Increased susceptibility to UC in an individual does not mean the individual will necessarily develop UC. However, increased susceptibility to UC in an individual is associated with an increased probability of having ulcerative colitis in the future.

The term "pANCA-reactive fragment," as used in reference to histone H1, a histone H1-like antigen, a porin antigen or a Bacteroides antigen, means a peptide or polypeptide portion of the antigen that has pANCA-reactive activity as defined by the ability to form a complex with pANCA. Thus, the term "pANCA-reactive fragment of histone H1," as used herein, means a peptide or polypeptide that has an amino acid sequence having at least 80% identity to a portion of one of the amino acid sequences shown in FIG. 1 and pANCA-reactive activity as defined by the ability to form a complex with pANCA. A pANCA-reactive fragment can have from about three amino acids to about 200 amino acids. Preferably, a pANCA-reactive fragment of one of the UC pANCA antigens disclosed herein has from about five to about fifty amino acids and most preferably from about eight to about twenty amino acids.

Several pANCA-reactive fragments of histone H1 are disclosed herein. As set forth in Examples II and III, peptides SEQ ID NO: 13, SEQ ID NO: 14 and SEQ ID NO: 20 are pANCA-reactive fragments of histone H1, identified by their reactivity with NANUC-1 and NANUC-2. Thus, pANCA-reactive fragments of histone H1 can include, for example, the amino acid sequence of SEQ ID NO: 7, SEQ ID NO: 13, SEQ ID NO: 14 or SEQ ID NO: 20. A pANCA-reactive fragment of histone H1 can have, for example, the amino acid sequence Pro-Lys-Lys-Ala-Lys-Lys-Pro-Ala-Ala-AlaThr-Val-Thr-Lys-Lys (SEQ ID NO: 20).

As disclosed herein, a pANCA-reactive fragment of histone H1 can be, for example, SEQ ID NO: 34 (amino acids 160–174 of H1.5); SEQ ID NO: 35 (amino acids 170 to 184 of H1.5) or SEQ ID NO: 36 (amino acids 180–194 of H1.5). As also disclosed herein, a pANCA-reactive fragment of histone H1 can be SEQ ID NO: 37 (amino acids 172 to 184 of H1.5); SEQ ID NO: 38 (amino acids 69 to 184 of H1.5); SEQ ID NO: 39 (amino acids 69 to 171 of H1.5); SEQ ID NO: 40 (amino acids 69 to 226 of H1.5); or SEQ ID NO: 41 (amino acids 172 to 226 of H1.5), which were identified as pANCA-reactive fragments of histone H1 by their reactivity with NANUC-2 (see Example IV). Reactivity of pANCA antibody with these fragments indicates that a pANCA reactive fragment of histone H1 can have an epitope within or around amino acids 172 to 184 of histone H1.5 (SEQ ID NO: 37). An additional UC pANCA epitope can be localized to amino acids 69 to 171 of histone H1.5, as shown by the reactivity of SEQ ID NO: 39 with NANUC-2.

A pANCA-reactive fragment of an antigen disclosed herein can be identified by the ability to form a complex with pANCA. For example, a pANCA-reactive fragment of histone H1, a histone H1-like antigen, a porin antigen or a Bacteroides antigen can be identified by its ability to form a complex with pANCA when contacted with pANCA-positive UC sera. Assays for the formation of an antigen-pANCA complex using pANCA-positive sera are well known in the art. For example, an enzyme-linked immunosorbent assay (ELISA) as described in Saxon et al., *J. Allergy Clin. Immunol.* 86:202–210 (1990), which is incorporated herein by reference, is particularly useful in identifying a pANCA-reactive fragment that forms a complex with pANCA.

A pANCA-reactive fragment of histone H1, a histone H1-like antigen, a porin antigen or a Bacteroides antigen further can be identified by its ability to form a complex with a representative UC pANCA monoclonal antibody, such as NANUC-2. The sequences of the NANUC-2 heavy and light chains are provided herein, and assays for determining binding to NANUC-2 are described in Examples IA and IB. An ELISA assay, for example, is particularly useful in identifying a pANCA-reactive fragment. Example II describes identification of the pANCA-reactive fragments of histone H1 SEQ ID NO: 13 and SEQ ID NO: 14, and Example II describes identification of the pANCA-reactive fragment SEQ ID NO: 20 using ELISA analysis. One skilled in the art understands that a pANCA-reactive fragment of a histone H1-like antigen, a porin antigen or a Bacteroides antigen can be similarly identified.

The histone H1, histone H1-like, porin and Bacteroides antigens of the invention also can be useful in treating UC. The present invention provides, for example, methods of inducing tolerance in a pANCA-positive patient with UC by administering an effective dose of histone Hal or tolerogenic fragment thereof, to the pANCA-positive patient with UC. A tolerogenic fragment of histone H1 useful in the methods of the invention can include, for example, the amino acid sequence of SEQ ID NO: 7, SEQ ID NO: 13, SEQ ID NO: 14 or SEQ ID NO: 20. A particularly useful tolerogenic fragment of histone H1 includes the amino acid sequence of SEQ ID NO: 20. A tolerogenic fragment of histone H1 can be, for example, a 15-mer having amino acid sequence Pro-Lys-Lys-Ala-Lys-Lys-Pro-Ala-Ala-Ala-Thr-Val-Thr-Lys-Lys (SEQ ID NO: 20).

The invention also provides methods of inducing tolerance in a pANCA-positive patient with UC by administering to the patient an effective dose of a histone-like H1 antigen, or tolerogenic fragment thereof. Such a histone H1-like antigen can be, for example, a protein immunoreactive with NANUC-2 and having an amino acid sequence having at least 65% amino acid identity with SEQ ID NO: 27.

The invention also provides methods of inducing tolerance in a pANCA-positive patient with UC by administering to the patient an effective dose of a porin antigen, or tolerogenic fragment thereof. Such a porin antigen can be, for example, a protein immunoreactive with NANUC-2 and having at least 65% amino acid identity with SEQ ID NO: 28, SEQ ID NO: 29 or SEQ ID NO: 30.

The invention also provides methods of inducing tolerance in a pANCA-positive patient with UC by administering to the patient an effective dose of a Bacteroides antigen, or tolerogenic fragment thereof. Such a Bacteroides antigen can be, for example, a *Bacteroides cecae* protein immunoreactive with NANUC-2 and having a molecular weight of about 100 kDa by SDS-PAGE electrophoresis.

The term "tolerogenic fragment," as used in reference to histone H1, a histone H1-like antigen, a porin antigen or a Bacteroides antigen, means a peptide or polypeptide portion of the antigen that has tolerogenic activity as defined by its ability either alone, or in combination with another molecule, to produce a decreased immunological response. For example, the term "tolerogenic fragment of histone H1," as used herein, means a peptide or polypeptide which has an amino acid sequence having at least 80% identity to a portion of one of the amino acid sequences shown in FIG. 1 and tolerogenic activity as defined by its ability either alone, or in combination with another molecule, to produce a decreased immunological response. A tolerogenic fragment of histone H1, a histone H1-like antigen, a porin antigen or a Bacteroides antigen has from about three amino acids to about 200 amino acids. Preferably, a tolerogenic fragment of histone H1, a histone H1-like antigen, a porin antigen or a Bacteroides antigen has from about five to about fifty amino acids and most preferably from about eight to about twenty amino acids.

A particularly useful tolerogenic fragment of histone H1, a histone H1-like antigen, a porin antigen or a Bacteroides antigen can be a cryptic T-cell determinant that normally is not the target of T-cell recognition due to inefficient processing and antigen presentation (see, for example, Sercarz et al., *Ann. Rev. Immunol.* 11:729 (1993), which is incorporated herein by reference). Without wishing to be bound by the following, ulcerative colitis can be associated with an immune response to histone H1 in disease tissue due to expression of a normally cryptic histone H1 T-cell determinant in an immunogenic form in disease target tissues but not in other tissues.

As disclosed herein, a variety of cell types have substantial amounts of NANUC-2 reactive histone H1, as assayed by Western analysis which involves denatured histone H1. In particular, all cell types assayed by Western analysis, including both hematopoietic and non-hematopoietic cells such as neutrophils, lymphocytes, Molt-4, HL60 promyelocytic leukemia and COS cells, have NANUC-2 reactive histone H1. However, as disclosed herein, only neutrophils and HL60 cells are reactive with NANUC-2 or UC sera when cells are methanol-fixed and assayed by an immunohistochemical analysis involving native protein. These results indicate that native, but not denatured, histone H1 can have different immunoaccessibility properties in neutrophilic and non-neutrophilic cell types.

The cell-type specific immunoaccessibility of histone H1 is supported by polyclonal rabbit anti-histone H1 antisera directed against an N-terminal 35 amino acid fragment of human histone H1 isoform H1$^s$-2 (SEQ ID NO: 7). The antiserum against SEQ ID NO: 7 recognizes all histone H1 isoforms and has nearly identical reactivity profiles as NANUC-2 using Western analysis. Furthermore, the antisera against SEQ ID NO: 7, like pANCA-positive sera from UC patients, stains methanol-fixed neutrophils in a perinuclear distribution but not non-neutrophilic cells such as eosinophils or lymphocytes.

A tolerogenic fragment of histone H1, a histone H1-like antigen, a porin antigen or a Bacteroides antigen can be identified using a variety of assays, including in vitro assays such as T-cell proliferation or cytokine secretion assays and in vivo assays such as the induction of tolerance in murine models of ulcerative colitis. T-cell proliferation assays, for example, are well recognized in the art as predictive of tolerogenic activity (see, for example, Miyahara et al., *Immunol.* 86:110–115 (1995) or Lundin et al, *J. Exp. Med.* 178:187–196 (1993), each of which is incorporated herein by reference). A T-cell proliferation assay can be performed by culturing T-cells with irradiated antigen-presenting cells, such as normal spleen cells, in microtiter wells for 3 days with varying concentrations of a fragment of histone H1, a histone H1-like antigen, a porin antigen or a Bacteroides antigen to be assayed; adding $^3$H-thymidine; and measuring incorporation of $^3$H-thymidine into DNA. In such an assay, a fragment of histone H1, a histone H1-like antigen, a porin antigen or a Bacteroides antigen can be tested for activity, for example, at concentrations of 20 µg/ml and 40 µg/ml.

A tolerogenic fragment of histone H1, a histone H1-like antigen, a porin antigen or a Bacteroides antigen also can be identified using a T-cell cytokine secretion assay as is well known in the art. For example, T cells can be cultured with irradiated antigen-presenting cells in microtiter wells with varying concentrations of the fragment of interest and, after three days, the culture supernatants can be assayed for IL-2, IL-4 or IFN-γ as described in Czerinsky et al., *Immunol. Rev.* 119:5–22 (1991), which is incorporated herein by reference.

Primary T-cells for use in a T-cell proliferation assay or cytokine secretion assay, for example, can be isolated from lamina propria or peripheral blood. In addition, a convenient source of T-cells for use in an in vitro assay for tolerogenic activity can be a T-cell line established from an ulcerative colitis patient, murine model of ulcerative colitis or a healthy animal immunized with histone H1. A preferred source of T-cells for use in identifying a tolerogenic fragment of histone H1, a histone H1-like antigen, a porin antigen or a Bacteroides antigen is an ulcerative colitis patient.

A T-cell line can be established from a patient with UC, for example, by culturing T lymphocytes with about 1 µg/ml histone H1, which is prepared, for example, from human bone marrow as described in Example I, in the presence of low concentrations of growth-supporting IL-2 (about 10 µg/ml). A T-cell line can be established by culturing T lymphocytes with antigen-presenting cells and feeding the cells on an alternating four to five day cycle with either IL-2 and histone H1 or IL-2 alone as described in Nanda et al., *J. Exp. Med.* 176:297–302 (1992), which is incorporated herein by reference. A cell line that develops into a reliably proliferating cell line dependent on the presence of histone H1 is particularly useful in identifying tolerogenic fragments of histone H1. The establishment of T-cell lines from small intestinal mucosa is described, for example, in Lundin et al., supra, 1993. T cell lines dependent upon the presence of a histone H1-like antigen, a porin antigen or a Bacteroides antigen can be prepared similarly and used to identify tolerogenic fragments of a histone H1-like antigen, a porin antigen or a Bacteroides antigen, respectively.

A tolerogenic fragment of histone H1, a histone H1-like antigen, a porin antigen or a Bacteroides antigen can also be identified by its ability to induce tolerance in vivo, as indicated by a decreased immunological response, which can be a decreased T-cell response, such as a decreased proliferative response or cytokine secretion response as described above, or a decreased antibody titer to the antigen. A neonatal or adult mouse can be tolerized with a fragment of histone H1, for example, and a T-cell response or anti-histone H1 antibody titer can be assayed after challenging by immunization. For example, a neonatal mouse can be tolerized within 48 hours of birth by intraperitoneal administration of about 100 µg of a fragment of histone H1 emulsified with incomplete Freund's adjuvant and subsequently immunized with histone H1 at about 8 weeks of age (see, for example, Miyahara, supra, 1995). An adult mouse can be tolerized intravenously with about 0.33 mg of a fragment of histone H1, administered daily for three days (total dose 1 mg), and immunized one week later with histone H1. A decreased T-cell response, such as decreased proliferation or cytokine secretion, which indicates tolerogenic activity, can be measured using T-cells harvested 10 days after immunization. In addition, a decreased anti-histone H1 antibody titer, which also indicates tolerogenic activity, can be assayed using blood harvested 4–8 weeks after immunization. Methods for assaying a T-cell response or anti-histone H1 antibody titer are described above and are well known in the art. Neonatal or adult mice can be tolerized similarly with a histone H1-like antigen, a porin antigen, or a Bacteroides antigen and used to identify tolerogenic fragments of the histone H1-like antigen, the porin antigen or the Bacteroides antigen, respectively.

A tolerogenic fragment of histone H1, a histone H1-like antigen, a porin antigen or a Bacteroides antigen also can be identified using a murine model of ulcerative colitis. Neonatal or adult mice having ulcerative colitis-like disease can be tolerized with a fragment of histone H1, a histone H1-like antigen, a porin antigen or a Bacteroides antigen as described above, and the T-cell response or anti-histone antibody titer assayed. A decreased T-cell response or decreased antibody titer to the antigen indicates a decreased immunological response and, thus, serves to identify a tolerogenic fragment of histone H1, the histone H1-like antigen, porin antigen or Bacteroides antigen. In addition, a tolerogenic fragment of histone H1, a histone H1-like antigen, a porin antigen or a Bacteroides antigen can be identified by the ability to reduce the frequency, time of onset or severity of colitis in a murine model of UC.

Several well-accepted murine models of ulcerative colitis are useful in identifying a tolerogenic fragment of histone H1 or another UC pANCA antigen disclosed herein. For example, mice deficient in IL-2 as described in Sadlack et al., *Cell* 75:253–261 (1993), which is incorporated herein by reference, and mice deficient in IL-10 as described in Kuhn et al., *Cell* 75:263–274 (1993), which is incorporated herein by reference, have ulcerative-colitis like disease and are useful in identifying a tolerogenic fragment of histone H1, a histone H1-like antigen, a porin antigen or a Bacteroides antigen. Furthermore, mice with mutations in T cell receptor (TCR) α, TCR α, TCR β×δ, or the class II major histocompatiblility complex (MHC) as described in Mombaerts et al., *Cell* 75:275–282 (1993), which is incorporated herein by reference, develop inflammatory bowel disease that resembles ulcerative colitis and, thus, are useful in identifying a tolerogenic fragment of histone H1, a histone H1-like antigen, a porin antigen or a Bacteroides antigen. Similarly, a fragment can be assayed for tolerogenic activity in a SCID mouse reconstituted with CD45RB CD4+ T-cells, which is a well-accepted model of human ulcerative colitis, as described in Powrie et al., *Immunity* 1:553–562 (1994), which is incorporated herein by reference. Thus, a tolerogenic fragment of histone H1, a histone H1-like antigen, a porin antigen or a Bacteroides antigen can be readily identified by an in vitro or in vivo assay disclosed herein or by another assay well known in the art.

A pANCA-reactive or tolerogenic fragment can be identified by screening, for example, fragments of the antigen produced by chemical or proteolytic cleavage. A fragment prepared from histone H1 purified from a target tissue such as intestinal mucosa can be particularly useful since such a fragment can have a post-translational modification that contributes to pANCA-reactive activity or tolerogenic activity. Methods for chemical and proteolytic cleavage and for purification of the resultant protein fragments are well known in the art (see, for example, Deutscher, *Methods in Enzymology*, Vol. 182, "Guide to Protein Purification," San Diego: Academic Press, Inc. (1990), which is incorporated herein by reference). For example, a chemical such as cyanogen bromide or a protease such as trypsin, chymotrypsin, V8 protease, endoproteinase Lys-C, endoproteinase Arg-C or endoproteinase Asp-N can be used to produce convenient fragments of histone Hl, a histone H1-like antigen, a porin antigen or a Bacteroides antigen that can be screened for pANCA-reactive activity or tolerogenic activity using one of the assays disclosed herein.

A pANCA-reactive or tolerogenic fragment of histone H1, a histone H1-like antigen, a porin antigen or a Bacteroides antigen also can be identified by screening a large collection, or library, of random peptides or peptides of interest for pANCA-reactive activity or tolerogenic activity. Peptide libraries include, for example, tagged chemical libraries comprising peptides and peptidomimetic molecules. Peptide libraries also comprise those generated by phage display technology. Phage display technology includes the expression of peptide molecules on the surface of phage as well as other methodologies by which a protein ligand is or can be associated with the nucleic acid which encodes it. Methods for production of phage display libraries, including vectors and methods of diversifying the population of peptides which are expressed, are well known in the art (see, for example, Smith and Scott, *Methods Enzymol*. 217:228–257 (1993); Scott and Smith, *Science* 249:386–390 (1990); and Huse, WO 91/07141 and WO 91/07149, each of which is incorporated herein by reference). These or other well known methods can be used to produce a phage display library which can be screened, for example, with one of the disclosed assays for pANCA-reactive activity or tolerogenic activity. If desired, a population of peptides can be assayed for activity en masse. For example, to identify a pANCA-reactive fragment of histone H1, a histone H1-like antigen, a porin antigen or a Bacteroides antigen, a population of peptides can be assayed for the ability to form a complex with NANUC-2; the active population can be subdivided and the assay repeated in order to isolate a pANCA-reactive fragment from the population.

In addition, a peptide library can be a panel of peptides spanning the entire sequence of an antigen of interest. For example, a panel of about 75 individual 15-mer peptides spanning the sequence of human histone H1 isoform $H1^s$-2 (SEQ ID NO: 2) can be synthesized, each overlapping by three residue shifts using the Mimotope cleavable pin technology (Cambridge Research Biochemicals, Wilmington, Del.), as described by Geysen et al., *Science* 235:1184 (1987), which is incorporated herein by reference. A panel of peptides spanning the sequence of any of the histone H1 isoforms such as those shown in FIG. 1 or another UC pANCA antigen disclosed herein can be generated similarly, and the panel screened for pANCA-reactive activity or tolerogenic activity using one of the assays described above (see, for example, Miyahara et al., supra, 1995, which is incorporated herein by reference).

A library of peptides to be screened also can be made up of peptides of interest, such as a population of peptides related in amino acid sequence to SEQ ID NO: 7 or SEQ ID NO: 20 but having one or more amino acids that differ from SEQ ID NO: 7 or SEQ ID NO: 20. For identifying a tolerogenic fragment of histone H1, peptides of interest also can be peptides derived from a histone H1 sequence that have appropriate HLA-DR binding motifs as described, for example, in Sette et al., *J. Immunol*. 151:3163–3170 (1993), which is incorporated herein by reference. A particularly useful population of peptides is a population having a HLA-DR2 binding motif (Yang et al., supra, 1993). If desired, peptides of interest can be selected for HLA-DR binding activity as described in Sette et al., supra, 1993, prior to screening for tolerogenic activity.

As used herein, the term "fragment" means a peptide, polypeptide or compound containing naturally occurring amino acids, non-naturally occurring amino acids or chemically modified amino acids. A pANCA-reactive or tolerogenic fragment of histone H1, a histone H1-like antigen, a porin antigen or a Bacteroides antigen also can be a peptide mimetic, which is a non-amino acid chemical structure that mimics the structure of a peptide having an amino acid sequence, provided that the peptidomimetic retains pANCA-reactive activity or tolerogenic activity, as defined herein. Such a mimetic generally is characterized as exhibiting similar physical characteristics such as size, charge or hydrophobicity in the same spatial arrangement found in its peptide counterpart. A specific example of a peptide mimetic is a compound in which the amide bond between one or more of the amino acids is replaced, for example, by a carbon-carbon bond or other bond well known in the art (see, for example, Sawyer, *Peptide Based Drug Design*, ACS, Washington (1995), which is incorporated herein by reference).

As used herein, the term "amino acid" refers to one of the twenty naturally occurring amino acids, including, unless stated otherwise, L-amino acids and D-amino acids. The term amino acid also refers to compounds such as chemically modified amino acids including amino acid analogs, naturally occurring amino acids that are not usually incorporated into proteins such as norleucine, and chemically synthesized compounds having properties known in the art to be characteristic of an amino acid, provided that the compound can be substituted within a peptide such that it retains pANCA-reactive activity or tolerogenic activity. Examples of amino acids and amino acids analogs are listed in Gross and Meienhofer, *The Peptides: Analysis, Synthesis, Biology*, Academic Press, Inc., New York (1983), which is incorporated herein by reference. An amino acid also can be an amino acid mimetic, which is a structure that exhibits substantially the same spatial arrangement of functional groups as an amino acid but does not necessarily have both the α-amino and α-carboxyl groups characteristic of an amino acid.

A pANCA-reactive or tolerogenic fragment of histone H1, a histone H1-like antigen, a porin antigen or a Bacteroides antigen useful in the invention can be produced or synthesized using methods well known in the art. Such methods include recombinant DNA methods and chemical synthesis methods for production of a peptide. Recombinant methods of producing a peptide through expression of a nucleic acid sequence encoding the peptide in a suitable host cell are well known in the art and are described, for example, in Sambrook et al., *Molecular Cloning: A Laboratory Manual*, 2nd Ed, Vols 1 to 3, Cold Spring Harbor Laboratory Press, New York (1989), which is incorporated herein by reference. Nucleic acids encoding histone H1 are available to one skilled in the art as described in Eick et al., *Eur. J. Cell. Biol.* 49:110–115 (1989); Albig et al., *Genomics* 10:940–948 (1991); Carozzi et al., *Science* 224:1115–1117 (1984); La Bella et al., *J. Biol. Chem.* 263:2115–2118 (1988); Cole et al., *Gene* 89:265–269 (1990); Cheng et al., *Proc. Natl. Acad. Sci. USA* 86:7002–7006 (1989); Yan et al., *J. Biol. Chem.* 262:17118–17125 (1987); and Brown and Sitman, *J. Biol. Chem.* 268:713–718 (1993), each of which is incorporated herein by reference.

A pANCA-reactive or tolerogenic fragment of histone H1, a histone H1-like antigen, a porin antigen or a Bacteroides antigen useful in the invention also can be produced by chemical synthesis, for example, by the solid phase peptide synthesis method of Merrifield et al., *J. Am. Chem. Soc.* 85:2149 (1964), which is incorporated herein by reference. Standard solution methods well known in the art also can be used to synthesize a pANCA-reactive or tolerogenic fragment useful in the invention (see, for example, Bodanszky, *Principles of Peptide Synthesis,* Springer-Verlag, Berlin (1984) and Bodanszky, *Peptide Chemistry,* Springer-Verlag, Berlin (1993), each of which is incorporated herein by reference). A newly synthesized peptide can be purified, for example, by high performance liquid chromatography (HPLC), and can be characterized using, for example, mass spectrometry or amino acid sequence analysis.

It is understood that limited modifications can be made to histone H1, a histone H1-like antigen, a porin antigen or a Bacteroides antigen without destroying its biological function. Similarly, limited modifications can be made to a pANCA-reactive fragment of an antigen disclosed herein or a tolerogenic fragment of an antigen disclosed herein without destroying its pANCA-reactive activity or tolerogenic activity. A modification of an antigen disclosed herein that does not destroy pANCA-reactive activity or a modification of an antigen disclosed herein that does not destroy tolerogenic activity is within the definition of such antigen. Similarly, a modification of a pANCA-reactive fragment of an antigen disclosed herein that does not destroy its ability to form a complex with pANCA is within the definition of a pANCA-reactive fragment of such antigen. Furthermore, a modification of a tolerogenic fragment of an antigen disclosed herein that does not destroy its ability to produce a decreased immunological response is within the definition of a tolerogenic fragment of such antigen. A modification can be, for example, an addition, deletion, or substitution of amino acid residues; substitution of a compound that mimics amino acid structure or function; or addition of chemical moieties such as amino or acetyl groups. The activity of a modified antigen disclosed herein or a modified fragment of such antigen can be assayed, for example, using one of the assays for pANCA-reactive or tolerogenic activity disclosed herein.

A particularly useful modification of an antigen disclosed herein or a pANCA-reactive or tolerogenic fragment of such antigen is a modification that confers, for example, increased stability. Incorporation of one or more D-amino acids is a modification useful in increasing stability of a protein or protein fragment. Similarly, deletion or substitution of lysine can increase stability by protecting against degradation. For example, such a substitution can increase stability and, thus, bioavailability of an antigen disclosed herein or a tolerogenic fragment of such antigen, provided that the substitution does not affect tolerogenic activity.

As used herein, the term "effective dose" means the amount of histone H1, a histone H1-like antigen, a porin antigen or a Bacteroides antigen, or a tolerogenic fragment thereof, useful for inducing tolerance in a pANCA-positive patient with UC. For induction of oral tolerance, for example, multiple smaller oral doses can be administered or a large dose can be administered. Such doses can be extrapolated, for example, from the induction of tolerance in animal models (see, for example, Trentham et al., *Science* 261:1727–1730 (1993), which is incorporated herein by reference).

The present invention also provides tolerogenic compositions that contain a UC pANCA antigen and are useful in inducing tolerance in a patient with UC. In particular, the invention provides a composition of histone H1, or fragment thereof, and a tolerogizing molecule. A composition of the invention can contain a fragment of histone H1 including the amino acid sequence of SEQ ID NO: 7, SEQ ID NO: 13, SEQ ID NO: 14 or SEQ ID NO: 20 combined with a tolerogizing molecule. A composition of the invention also can contain a fragment of histone H1 having the amino acid sequence of SEQ ID NO: 20 combined with a tolerogizing molecule.

The present invention also provides a composition of histone H1-like antigen, or tolerogenic fragment thereof, combined with a tolerogizing molecule. In such a composition, a histone H1-like antigen can be, for example, a protein having an amino acid sequence having at least 65% amino acid identity with SEQ ID NO: 27.

In addition, there is provided a porin antigen, or tolerogenic fragment thereof, combined with a tolerogizing molecule. In a composition of the invention, a porin antigen can be, for example, a protein having at least 65% amino acid identity with SEQ ID NO: 28, SEQ ID NO: 29 or SEQ ID NO: 30.

Also provided herein is a composition containing a Bacteroides antigen, or a tolerogenic fragment thereof, combined with a tolerogizing molecule. Such a Bacteroides antigen can be, for example, a *Bacteroides cecae* protein having a molecular weight of about 100 kDa by SDS-PAGE electrophoresis.

Various molecules are known in the art to cause, promote or enhance tolerance. See, for example, U.S. Pat. No. 5,268,454, and citations therein, which are incorporated herein by reference. As used herein, the term "tolerogizing molecule" means a molecule, compound or polymer that causes, promotes or enhances tolerogenic activity when combined with histone H1, a histone H1-like antigen, a porin antigen or a Bacteroides antigen, or fragment thereof. A tolerogizing molecule can be, for example, conjugated to histone H1 or another UC pANCA antigen. Such tolerogizing molecules include, for example, polyethylene glycol and are well known in the art (see, for example, U.S. Pat. No. 5,268,454, supra).

An effective dose of histone H1, a histone H1-like antigen, a porin antigen, or a Bacteroides antigen or a tolerogenic fragment thereof for inducing tolerance can be administered by methods well known in the art. Oral tolerance is well-recognized in the art as a method of treating autoimmune disease (see, for example, Weiner, *Hospital Practice*, pp. 53–58 (Sept. 15, 1995), which is incorporated herein by reference). For example, orally administered autoantigens suppress several experimental autoimmune models in a disease- and antigen-specific fashion; the diseases include experimental autoimmune encephalomyelitis, uveitis, and myasthenia, collagen- and adjuvant-induced arthritis, and diabetes in the NOD mouse (see, for example, Weiner et al., *Ann. Rev. Immunol.* 12:809–837 (1994), which is incorporated herein by reference). Furthermore, clinical trials of oral tolerance have produced positive results in treating multiple sclerosis, rheumatoid arthritis and uveitis. In addition, parenteral administration of histone H1, another antigen of the invention, or a tolerogenic fragment thereof, can be used to induce tolerance. Subcutaneous injection, for example, can be used to deliver histone H1, a histone H1-like antigen, a porin antigen or a Bacteroides antigen, or a tolerogenic fragment thereof, to a pANCA-positive patient with UC (Johnson, *Ann. Neurology* 36(suppl.):S115–S117 (1994), which is incorporated herein by reference).

The invention also provides methods of preventing UC in an individual by administering an effective dose of histone H1, a histone H1-like antigen, a porin antigen or a Bacteroides antigen, or a tolerogenic fragment thereof, to the individual. The methods of the invention are particularly useful for preventing UC in an individual having increased susceptibility to UC. Such methods can be particularly useful for preventing UC when an effective dose of the antigen or tolerogenic fragment is administered to a newborn individual.

Prior to this time, a connection between specific enteric bacteria and UC has not been made although bacteria have been shown to play a role in the pathogenesis of other enteric diseases. For example, *H. pylori* has been implicated in the pathogenesis of peptic ulcer disease. Antibiotics against *H. pylori* have been shown to effectively treat this disease (see, for example, Sontag, *Am. J. Gastroenterol.* 92:1255–1261 (1997); and Pipkin et al., *Helicobactor.* 2:159–171 (1997), each of which is incorporated herein by reference). As disclosed herein, several colonic bacteria harbored in UC patients, including bacteria from the genera of Mycobacteria, Escherichia and Bacteroides, express antigens reactive with the pANCA autoantibody, which is present in the majority of patients with UC (see Examples V and VI). These results indicate that an agent directed against one or more of such pANCA-reactive bacteria can be useful in reducing the number of colonic bacteria, thereby diminishing the immune stimulus contributing to UC and ameliorating the symptoms of the disease.

Thus, the invention provides a method of identifying an agent useful for treating UC by obtaining a sample of enteric bacteria from a patient with UC; isolating from the sample a bacterial species that expresses a pANCA-reactive antigen; contacting the bacterial species with an agent; and assaying for the reduced growth or viability of the bacterial species, where the reduced growth or viability of the bacterial species indicates that the agent is an agent useful for treating UC. The enteric bacterial species that expresses a pANCA-reactive antigen can be, for example, a member of the genera of Mycobacteria, Escherichia or Bacteroides. An enteric Mycobacteria that expresses a pANCA-reactive antigen can be, for example, *Mycobacterium tuberculosis, Mycobacterium bovis, Mycobacterium smegmatis* [1-2c], *Mycobacterium avium* and *Mycobacterium avium paratuberculosis*. An enteric Escherichia that expresses a pANCA-reactive antigen can be, for example, *Escherichia coli*. An enteric Bacteroides that expresses a pANCA-reactive antigen can be, for example, *Bacteroides cecae*. One skilled in the art understands that the bacterial specieis which is contacted with an agent in the methods of the invention can be a single bacterial species or can be a mixture of two or more bacterial species that express a pANCA-reactive antigen.

As used herein, the term "agent" means a biological or chemical compound such as a simple or complex organic molecule, a peptide, a protein, an antibody, a lipid or an oligonucleotide.

As used herein, the term "agent useful for treating UC" means an agent that can reduce the viability or growth of a bacterial species that expresses a pANCA-reactive antigen. Thus, an agent useful for treating UC is an agent that functions as a bacteristat or bactericide against a bacterial species that expresses a pANCA-reactive antigen. An agent useful for treating UC can be a bacterial antibiotic, which is a molecule that is produced by a microorganism or a plant, or a close chemical derivative of such a molecule, that can reduce the growth or viability of a bacterial species that expresses a pANCA-reactive antigen. An agent useful for treating UC can function by a variety of mechanisms, for example, by inhibiting bacterial protein synthesis, inhibiting bacterial DNA synthesis, inhibiting the synthesis of a bacterial cell wall or inhibiting synthesis of an essential nutrient of a bacterial species that expresses a pANCA-reactive antigen. Such an agent can selectively reduce the viability or growth of a particular bacterial species that expresses a pANCA-reactive antigen. An agent useful for treating UC also can have activity in reducing the growth or viability of a broad spectrum of bacteria such as a genus of bacteria. One skilled in the art understands that, preferably, an agent useful for treating UC reduces the growth or viability of a bacterial specieis that expresses a pANCA-reactive antigen without significantly altering the growth or viability of mammalian cells, especially human cells.

The following examples are intended to illustrate but not limit the present invention.

EXAMPLE I

Identification of the Ulcerative Colitis pANCA Target Antigen

This example demonstrates that representative UC pANCA monoclonal antibodies bind histone H1 specifically.

A. Histone H1 is an Ulcerative Colitis pANCA Target Antigen

Representative UC pANCA monoclonal antibodies, designated NANUC-1 and NANUC-2, were isolated from a UC lamina propria lymphocyte phage display IgG library and use to screen human neutrophil. Western analysis demonstrated specific binding of NANUC-2 to a nuclear protein doublet of 32–33 kDa. Purification by subcellular fractionation and preparative gel electrophoresis followed by protein microsequencing identified the NANUC-2 reactive antigen as histone H1.

Western analysis showed reactivity with lysine-rich calf thymus histone. In addition, histones purified from human neutrophil were fractionated into a perchloric acid insoluble fraction (containing core histones) and a perchloric acid soluble fraction (containing histone H1). As shown in FIG. 2, NANUC-2 reacted with the perchloric acid soluble histone fraction, indicating that histone H1 is an ulcerative colitis pANCA target antigen. Purified core histones (H2A, H2B, H3 and H4) were minimally reactive with NANUC-2. In addition, purified human histone H1 isoforms $H1^s$-1, $H1^s$-2, $H1^s$-3, $H1^s$-4 and $H1^o$ were analyzed by immunoblot analysis, and NANUC-2 was reactive with each of the isoforms including H1.

Histone H1 was purified according to the methods described in Prescott, *Methods in Cell Biology*, Vol XVI, "Chromatin and Chromosomal Protein Research" (New York, N.Y.: Academic Press (1977)), which is incorporated herein by reference, as follows. Purified bone marrow was obtained and red blood cell lysed prior to freezing. The bone marrow, which contained lymphocytes and granulocytes, was thawed rapidly and washed with phosphate-buffered saline (PBS). The cells were extracted with four cell volumes of 200 mM $H_2SO_4$/40 mM $NaHSO_3$ in the presence of protease inhibitors, sonicated for 60 seconds on ice, and incubated on ice for one hour with occasional vortexing. Nuclei and cell debris were pelleted at 2500 rpm (Beckman JA-6) at 19194° C. for 20 minutes, the supernatant transferred to a new tube, and core histones (H2A, H2A, H3 and H4) precipitated at −20° C. overnight by the addition of three to four volumes of 95% ethanol. The histone pellet was washed with 70% ethanol, dried and resuspended in 3 ml 40 mM $NaHSO_3$ with protease inhibitors.

Histone H1 was selectively extracted from core histones by addition of 70% perchloric acid (to a final concentration of 5%) followed by incubation on a rotating wheel at 4° C. for 1 hour. Core histones were pelleted at 2500 rpm at 4° C. for 20 minutes. Histone H1 was precipitated from the supernatant for 2 hours at −20° C. with 10 ml of acidified acetone (10 ml acetone+77 µl concentrated hydrochloric acid). Histone H1 was centrifuged as above, and the pellet washed with a solution of 3.5 ml acetone/1 ml 1M HCl to remove high-mobility group (HMG) proteins. The core histones and histone H1 pellets each were washed separately three times with 5 ml 95% ethanol and dried. Protein purity was established by polyacrylamide gel electrophoresis and Coomassie blue staining.

Western analysis was performed as follows. Cells were lysed in 10 mM HEPES/1.5 mM $MgCl_2$/10 mM KCl pH7.9 in the presence of protease inhibitors and sheared with a 20G needle. Lysis was monitored by trypan blue exclusion. Nuclei were pelleted and resuspended in extraction buffer, and the cell fractions electrophoresed on a 12% polyacrylamide gel under non-reducing conditions. Proteins were transferred to nitrocellulose membranes, and the transfer verified by Ponceau S red staining (SIGMA, St. Louis, Mo.). Membranes were blocked with 5% milk in 0.1% Tween-20/PBS for 1 hour. Primary and secondary antibody incubations were for 1 hour in 1% milk in 0.1% Tween-20/PBS. The primary antibodies, NANUC-1, NANUC-2, and anti-tetanus toxoid Fabs were used at a concentration of 0.1 to 1.0 µg/ml. The secondary antibody was goat anti-human Fab-alkaline phosphatase or goat anti-human kappa-biotin used at a dilution of 1 to 1000 or 1 to 2000, respectively. Alkaline phosphatase labeled antibodies were detected with BCIP-NBT (SIGMA). Biotinylated antibodies were detected with SA-HRP (Amersham Lifesciences, Inc., Arlington Heights, Ill.) and enhanced chemiluminescence.

B. Reactivity of NANUC-2 with Histone H1 Using ELISA Analysis

Microtiter plates coated with neutrophil, total histone or purified calf thymus histone H1 were used for ELISA analysis as described below. The reactivity of NANUC-1, NANUC-2 and negative control anti-tetanus toxoid antibody was tested against human PMN (neutrophil), total histone, calf thymus histone H1, or tetanus toxoid antigen. As shown in FIG. 3, the ELISA assays demonstrated that NANUC-1 and NANUC-2 react with human neutrophil. However, NANUC-2, but not NANUC-1 or anti-tetanus toxoid antibody, was reactive with total calf thymus histone (histone H1 and core histones) and calf thymus histone H1 (SIGMA).

ELISA assays were performed as follows. For detection of total Fab immunoglobulin, microtiter plates (Costar 3069, Cambridge, Mass.) were coated overnight at 4° C. with 500 ng/well antigen in bicarbonate pH 9.6 coating buffer. Wells were blocked with 0.25% BSA/PBS for 1 hour, incubated with rFabs diluted in 0.25% BSA/PBS for 1 hour, and washed five times with 0.5% Tween-20/PBS at room temperature. Plates were subsequently incubated with a 1 to 1000 dilution of alkaline phosphatase-labeled goat anti-human Fab (Pierce, Rockford, Ill.) for 1 hour; washed five times in 0.5% Tween-20/PBS; washed three times with Tris-NaCl (50 mM Tris 150 mM NaCl pH 7.5); and developed with 5 mg/ml p-nitrophenyl phosphate (SIGMA) in 10% diethanolamine/1 mM $MgCl_2$ pH 9.8. The absorbance of each sample was measured at 405 nm using a Biorad ELISA reader (Richmond, Calif.). Neutrophil samples were prepared as described in Saxon et al., supra, 1990; total calf thymus histone and calf thymus histone H1 were obtained from SIGMA.

C. Reactivity of NANUC-2 with Subcellular Fractions

Figure 4A:
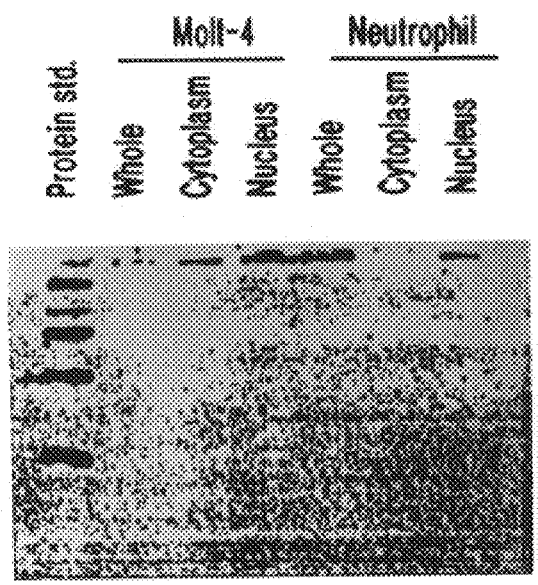
FIG. 4 shows Western analysis of whole cell, nuclear and cytoplasmic fractions of Molt-4 cells and human neutrophils. Identical blots were reacted with NANUC-1 or NANUC-2 or with negative control anti-tetanus toxoid antibody.
Figure 4B:
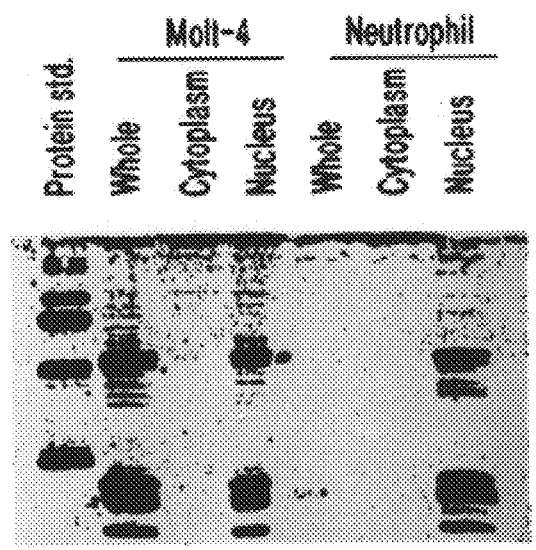
Figure 4C:
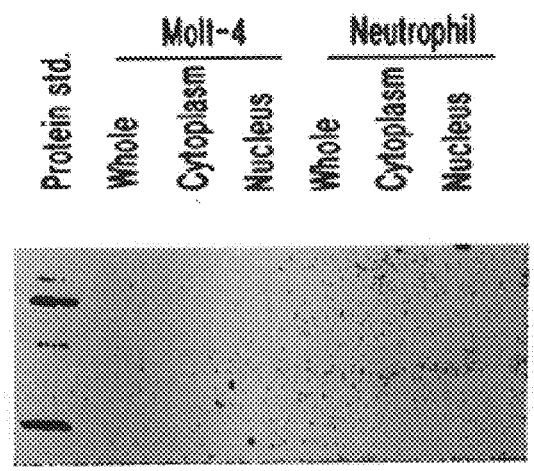

Subcellular fractionation of human neutrophils demonstrated that NANUC-2 is almost exclusively reactive with a nuclear protein doublet of 32–33 kDa apparent molecular weight (see FIG. 4). The NANUC-2 reactive doublet was present in the nuclear fraction of neutrophils and represents histone H1 subtypes $H1^s$-1, $H1^s$-2, $H1^s$-3, $H1^s$-4 and H1 as determined by apparent size on SDS-PAGE following Western blot detection. Additional lower molecular weight proteins, which have slight reactivity with NANUC-2, may represent the core histones or histone H1 degradation products. NANUC-1 and the negative control anti-tetanus toxoid antibody were not reactive with any protein species on Western blots.

In cell types other than neutrophils, histone H1 reactivity was detected in both whole cell lysate and nuclear fraction but not in the cytoplasmic fraction. In contrast, neutrophil nuclear fraction revealed a large amount of NANUC-2 reactive histone H1, but no reactivity was seen in whole cell lysate prepared from the same cells. The lack of reactivity in neutrophil whole cell lysate can be a result of very rapid degradation of histone H1 by proteases found in neutrophilic granules but not in other cells such as Molt-4 cells (see FIG. 4).

EXAMPLE II

Identification of pANCA-Reactive H1 Fragments

This example demonstrates that particular fragments of histone H1 are reactive with the NANUC-2 antibody.

To further characterize the pANCA-reactive histone H1 epitope, purified protein was subjected to chemical cleavage with N-N bromosuccinamide (NBS) and proteolysis with chymotrypsin, and reactivity of the resulting fragments was analyzed by silver staining and immunoblotting. NBS cleavage of H1 resulted in two fragments: an N-terminal 73 amino acid fragment (SEQ ID NO: 12) and a C-terminal 147 amino acid fragment (SEQ ID NO: 13). Because of the extremely charged nature of these fragments, the apparent mobilities of the 73 and 147 amino acid fragments are 23 and 11 kD, respectively. Immunoblot analysis revealed that only the larger 147 amino acid fragment (SEQ ID NO: 13) was reactive with NANUC-2, indicating that a pANCA-reactive epitope lies within the carboxy-terminal 147 amino acids. Chymotrypsin digests the N-terminal portion of the 147 amino carboxy-terminal fragment, producing a fragment with an apparent molecular weight of 17 kD. Immunoblots of chymotrypsin-digested H1 revealed NANUC-2 reactivity only with the carboxy-terminal fragment, thereby narrowing the pANCA-reactive epitope to the carboxyterminal 113 amino acids (SEQ ID NO: 14). As a control to show that the nonreactive N-terminal fragments were properly transferred, the same blots showed reactivity with a rabbit anti-H1–3 polyclonal specific for the N-terminal fragment (see Parseghian et al., *Chromosoma* 103:198 (1994) and Parseghian et al., *Chrom. Res.* 1:127 (1993), each of which is incorporated herein by reference).

H1 epitopes were mapped using N-N bromosuccinamide and chymotrypsin proteolysis with a procedure modified from Parseghian et al., supra, 1993; Sherod et al., *J. Biol Chem.* 12:3923 (1974) and Costa et al., *Clin. Exp. Immunol.* 63: 608 (1986), each of which is incorporated herein by reference. Briefly, in a 10 μl reaction, 12 μg of bone marrow histone H1 was cleaved with 0.85 μg N—N bromosuccinamide (Sigma) in 0.9 N acetic acid. The reaction was terminated at varying time points by transferring 2.5 μL aliquots into 7.5 μl stop buffer (0.125 M Tris Cl pH 7.6 with 10.7 μg tyrosine (Sigma)). Chymotrypsin cleavage was performed in a 10 μl reaction volume by incubating 6 pg bone marrow histone H1 with 0.01 μg chymotrypsin (Boehringer Mannheim, Indianapolis, Ind.) in 0.1 M Tris-Cl pH 8.0, 10 mM CaCl. Reactions were stopped at various time points by addition of 1 μl 20 mM phenyl methyl sulfonyl fluoride (PMSF; Boehringer Mannheim), and 1.5 μg of NBS and chymotryptic H1 fragments diluted in Laemli buffer were run on 13% acrylamide gels using a Biorad mini gel apparatus, transferred to nitrocellulose, and immunoblotted as described above. Gels were silver stained using a Biorad silver stain kit (Biorad, Richmond, Calif.).

EXAMPLE III

Identification of pANCA-Reactive Peptides Derived from Histone H1

This example demonstrates that synthetic peptides spanning histone H1 can be assayed for NANUC-1 and NANUC-2 binding to identify pANCA-reactive peptides.

Overlapping 15-mer peptides that spanned the C-terminal 109 amino acids of the human H1$^s$-3 gene product with an N-terminal biotin were synthesized (P. Allen, Washington University, St. Louis). Each of the peptides overlapped adjacent peptide sequences by five amino acids except for peptide SEQ ID NO: 25. The eleven peptide sequences are shown in Table 2.

Peptides were tested for binding to 1.0, 3.0 and 10.0 μg/ml NANUC-1, NANUC-2 and negative control anti-tetanus toxoid antibody P313 (anti-TT). As shown in FIG. 5, peptide SEQ ID NO: 20 was distinguished among the 11 peptides assayed by significant binding to NANUC-1 and NANUC-2 (OD$_{405}$ of approximately 0.5; significant at 1.0 μg/ml) compared to background levels observed with the rFab negative control anti-TT antibody, yielding an OD$_{405}$ of less than 0.1. Neither of the two adjacent, overlapping peptides SEQ ID NO: 19 or SEQ ID NO: 21 showed significant binding to both NANUC antibodies. Peptide SEQ ID NO: 17 also reacted with NANUC-1 and NANUC-1; however, this binding was weaker (OD$_{405}$ of approximately 0.25 for both NANUC antibodies) than the reactivity seen with peptide SEQ ID NO: 20.

TABLE 2

Histone H1 peptide sequences

| SEQ ID NO: | Amino acid sequence |
| --- | --- |
| SEQ ID NO: 15 | FKLNKKAASGEAKPK |
| SEQ ID NO: 16 | EAKPKVKKAGGTKPK |
| SEQ ID NO: 17 | GTKPKKPVGAAKKPK |
| SEQ ID NO: 18 | AKKPKKAAGGATPKK |
| SEQ ID NO: 19 | ATPKKSAKKTPKKAK |
| SEQ ID NO: 20 | PKKAKKPAAATVTKK |
| SEQ ID NO: 21 | TVTKKVAKSPKKAKV |
| SEQ ID NO: 22 | KKAKVAKPKKAAKSA |
| SEQ ID NO: 23 | AAKSAAKAVKPKAAK |
| SEQ ID NO: 24 | PKAAKPKVVKPKKAA |
| SEQ ID NO: 25 | KPKVVKPKKAAPKKK |

These data indicate that histone H1 peptide PKKAKKPAAATVTKK (SEQ ID NO: 20) is specifically reactive with two distinct UC pANCA monoclonal antibodies. Because adjacent peptides lack activity, the pANCA reactivity of peptide SEQ ID NO: 20 may depend on its unique internal linear amino acid sequence KPAAA (SEQ ID NO: 26) or may depend on the unique conformation of the peptide sequence SEQ ID NO: 20 in its entirety.

The eleven H1 peptides SEQ ID NOS: 15 to 25 were assayed for reactivity with UC pANCA monoclonal antibodies NANUC-1 and NANUC-2 as follows. ELISA wells were coated with 50 μl solution of the H1 peptide of interest (at a concentration of 250 μg/ml) in carbonate buffer, pH 9.6, overnight at 4° C. Wells were blocked with phosphate buffered saline/0.5% Tween-20/500 μg/ml bovine serum albumin (BSA; SIGMA) for 1 hour at room temperature. Wells were washed five times with 0.05% Tween-20 in PBS (wash buffer), then reacted with rfab antibody diluted in wash buffer at indicated concentrations for 2 hours at room temperature. Plates were washed five times, and immunocomplexes detected subsequently with 0.05% alkaline phosphatase-conjugated goat anti-human Fab (Pierce) in wash buffer for 1 hour at room temperature. After washing, the samples were reacted with BCIP-NBT substrate (SIGMA). FIG. 5 shows the absorbance at 405 nm (OD$_{405}$) after normalization for background binding due to reactivity with secondary antibody alone.

EXAMPLE IV

Identification of pANCA-Reactive Peptides Derived from Histone H1

This example demonstrates that fragments of histone H1 isoform H1.5 bind NANUC-2, thus identifying these fragments as pANCA-reactive fragments of histone H1.

Five recombinant fragments of human histone H1 isoform H1.5 (SEQ ID NO: 32) that spanned the C-terminal 158 amino acids of the H1.5 protein (amino acids 69 to 226 of SEQ ID NO: 32) with an N-terminal biotin were synthesized. The five fragments were as follows: SEQ ID NO: 37 (amino acids 172 to 184 of H1.5); SEQ ID NO: 38 (amino acids 69 to 184 of H1.5); SEQ ID NO: 39 (amino acids 69 to 171 of H1.5; SEQ ID NO: 40 (amino acids 69 to 226 of H1.5); and SEQ ID NO: 41 (amino acids 172 to 226 of H1.5).

Each of these five fragments bound selectively to NANUC-2 but did not bind to a control anti-tetanus toxoid antibody. The binding of SEQ ID NOS: 37, 38, 40 and 41 to NANUC-2 indicates the presence of a pANCA-reactive epitope of histone H1 that is in the region of amino acids 172 to 184 of histone H1.5. This region of histone isoform H1.5 is highly conserved among varying species and isoforms of histone H1 and is present, for example, in histone H1$^s$-3. The binding of SEQ ID NO: 39 to NANUC-2 indicates the presence of an additional pANCA-reactive epitope of histone H1 isoform H1.5 outside amino acids 172 to 184, within amino acids 69 to 171 of H1.5. In sum, these results demonstrate that histone H1 contains at least two distinct pANCA-reactive epitopes.

EXAMPLE V

Identification of Ulcerative Colitis pANCA Histone H1-Like Target Antigens

This example demonstrates that histone H1-like antigens present in a variety of Mycobacterial species are reactive with the NANUC-2 antibody.

A. A Mycobacterial Histone H1-Like Antigen is a pANCA Reactive Protein

BLAST analysis was used to search the microbial databases for linear peptide homologues of the C-terminal random coil domain of human histone H1 isoform H1.5 (SEQ ID NO: 32). This analysis revealed homologous sequences reported in the *M. turberculosis* genome database as anonymous open reading frames (ORFs).

In view of these homologous *M. turberculosis* ORFs, seven Mycobacterial strains from five Mycobacterial species were obtained from the American Type Culture Collection and from St. Mary's Hospital Medical School (London, UK). The Mycobacteria were grown using the media and growth conditions shown in FIG. 6. Whole cell extracts were prepared and analyzed by Western analysis using the NANUC-2 antibody essentially as described in Example I. As shown in FIG. 7, the NANUC-2 antibody detected a single 30–32 kDa protein, with a slightly varying size in each of the Mycobacterial species.

The pANCA-reactive 30–32 kDa protein from *M. avium paratuberculosis* was isolated by SDS-PAGE electrophoresis and PVDF membrane transfer. As shown in FIG. 8, the sequence of the first 18 amino acids of the N-terminal fragment (SEQ ID NO: 31) obtained by peptide sequencing was nearly identical to the amino-terminal sequence of a predicted protein of 214 amino acids from the *M. turberculosis* genome (SEQ ID NO: 27). The two amino acid differences in the N-terminal 18 amino acid sequence can reflect sequencing artifacts or sequence polymorphisms between *M. avium paratuberculosis* and *M. tuberculosis*. Alignment of the entire 214 amino acid *M. tuberculosis* protein (SEQ ID NO: 27) with human histone H1 isoform H1.5 (SEQ ID NO: 32) revealed 48% sequence similarity.

A nucleic acid encoding the *M. turberculosis* 214 amino acid histone H1-like protein (SEQ ID NO: 27) was cloned into an expression vector, and the expressed product analyzed. Immunoreactivity with NANUC-2 confirmed that this protein is a pANCA-reactive antigen. These results demonstrate that a histone H1-like antigen, such as Mycobacterial histone H1-like antigen of 30–32 kDa, can be a UC pANCA target antigen.

B. A Mycobacterial Histone H1-Like Antigen is Differentially Reactive with Normal and pANCA-positive UC Patient Sera Samples of human sera are taken from patients diagnosed with UC and from control normal individuals. Each UC sample is assayed against human PMN (neutrophil) for the presence of UC pANCA. pANCA-positive UC sera and normal sera are then assayed for reactivity against the *M. turberculosis* 214 amino acid histone H1-like antigen (SEQ ID NO: 27). The results show that a significantly greater percentage of UC pANCA-positive samples are reactive with the histone H1-like antigen as compared to the percentage of normal samples that react. These results demonstrate that a histone H1-like microbial protein can be a UC pANCA antigen useful in the diagnosis of ulcerative colitis.

EXAMPLE VI

Identification of Ulcerative Colitis pANCA Porin Target antigens

This example demonstrates that porin and Bacteroides antigens expressed by enteric bacteria from UC patients are reactive with the NANUC-2 antibody.

A. Enteric *E. coli* from UC Patients Express a pANCA-reactive Antigen

The disease-specific immune response exemplified by UC pANCA can be elicited by cross-reactive proteins of particular enteric bacteria. To isolate these bacteria, colonic biopsy specimens were obtained from three patients diagnosed with UC. The specimens were minced, and the colonic bacteria cultured using varying oxygen availability and culture media. After harvesting bacteria from the cultures, bacterial extracts were tested by Western analysis with the NANUC-2 antibody essentially as described above.

Cross-reactive proteins were only identified in the anaerobic cultures. The NANUC-2-reactive cultures were plated, and single colonies isolated and individually screened for UC pANCA antigen expression by Western analysis. Seven positive clones were isolated and identified by 16S rRNA sequencing essentially as described in Wilson and Blitchington, *Applied and Environ. Microbiol.* 62:2273–2278 (1996).

In particular, five clones were identified by 16S rRNA-typing as members of the *E. coli* species (P1Bc5, P1Bc9, P2c2, P2c5 and P2Lc2). As shown in FIG. 9, each of the five types of *E. coli* expressed a pANCA-reactive protein of about 35 kDa. These pANCA-reactive proteins could be divided into larger and smaller types, which were isolated by SDS-PAGE electrophoresis and PVDF membrane transfer. N-terminal amino acid sequencing of the larger and smaller pANCA-reactive proteins revealed an identical 19-mer peptide (SEQ ID NO: 33).

BLAST analysis revealed that this 19 amino acid sequence (SEQ ID NO: 33) is shared by a set of three closely related putative ORFs of the porin outer-membrane protein family (SEQ ID NOS: 28, 29 and 30; see FIG. 10). Shown in FIG. 11 is the CLUSTAL and BEST-FIT alignment of one such porin antigen (SEQ ID NO: 28) with histone H1.5 (SEQ ID NO: 32). This alignment reveals that porin antigens lack detectable linear sequence homology with histone H1.5 (SEQ ID NO: 32).

B. A Porin Antigen Expressed in *E. coli* is Differentially Reactive with Normal and UC pANCA-positive Patient Sera Samples of human sera are taken from patients diagnosed with UC and from control normal individuals. Each UC sample is assayed against human PMN (neutrophil) for the presence of UC pANCA. pANCA-positive UC sera and normal sera are then assayed for reactivity against the *E. coli* porin antigens described above (SEQ ID NOS: 28, 29 and 30). The results show that a significantly greater percentage of UC pANCA-positive samples are reactive with the porin antigen as compared to the percentage of normal samples that react. These results demonstrate that a porin antigen, such as one of the *E. coli* porin antigens described above (SEQ ID NOS: 28, 29 and 30), can be a UC pANCA antigen useful in the diagnosis of ulcerative colitis.

C. Enteric Bacteroides from UC Patients Express a UC pANCA-reactive Antigen

Two clones were identified by 16S rRNA-typing as described above as members of the *Bacteroides cecae* family (P2Lc3 and P2Lc5). As shown in FIG. 9B, these family members expressed a pANCA-reactive protein of about 100 kDa. Western analysis showed that the pANCA-reactive 100 kDa Bacteroides antigen was selectively expressed in Bacteroides but not expressed, for example, in *E. coli*.

D. An Antigen Expressed in Bacteroides is Differentially Reactive with Normal and UC pANCA-positive Patient Samples of human sera are taken from patients diagnosed with UC and from control normal patients. Each IUC sample is assayed against human PMN (neutrophil) for the presence of UC pANCA. pANCA-positive UC sera and normal sera are then assayed for reactivity against a protein of about 100 kDa that is isolated from *Bacteroides cecae* using SDS-PAGE electrophoresis and PVDF membrane transfer. The results show that a significantly greater percentage of UC pANCA-positive samples are reactive with the Bacteroides antigen as compared to the percentage of normal samples that react. These results demonstrate that a Bacteroides antigen, such as the 100 kDa antigen isolated from *Bacteroides cecae*, can be a UC pANCA antigen useful in the diagnosis of ulcerative colitis.

All journal article, reference and patent citations provided above, in parentheses or otherwise, whether previously stated or not, are incorporated herein by reference in their entirety.

Although the invention has been described with reference to the examples above, it should be understood that various modifications can be made without departing from the spirit of the invention. Accordingly, the invention is limited only by the following claims.

We claim:

1. A method of diagnosing ulcerative colitis (UC) in a subject suspected of having inflammatory bowel disease, comprising:
   (a) obtaining a sample from said subject;
   (b) contacting said sample with a histone H1-like antigen, or pANCA-reactive fragment thereof, under conditions suitable to form a complex of said histone H1-like antigen, or said pANCA-reactive fragment thereof, and antibody to said histone H1-like antigen; and
   (c) detecting the presence or absence of said complex, wherein said histone H1-like antigen comprises a protein immunoreactive with NANUC-2 and having an amino acid sequence having at least 70% amino acid identity with SEQ ID NO: 27, and wherein the presence of said complex indicates that said subject has UC.

2. The method of claim 1, wherein said histone H1-like antigen, or pANCA-reactive fragment thereof, is in isolated form.

3. The method of claim 1, wherein said histone H1-like antigen comprises a protein immunoreactive with NANUC-2 and having an amino acid sequence having at least 80% amino acid identity with SEQ ID NO: 27.

4. The method of claim 3, wherein said histone H1-like antigen, or pANCA-reactive fragment thereof, is in isolated form.

5. The method of claim 1, wherein said histone H1-like antigen comprises a protein immunoreactive with NANUC-2 and having an amino acid sequence having at least 90% amino acid identity with SEQ ID NO: 27.

6. The method of claim 5, wherein said histone H1-like antigen, or pANCA-reactive fragment thereof, is in isolated form.

7. The method of claim 1, wherein said histone H1-like antigen is a Mycobacterial antigen having a molecular weight of 30–32 kDa.

8. The method of claim 7, wherein said histone H1-like antigen, or pANCA-reactive fragment thereof, is in isolated form.

9. The method of claim 1, wherein said histone H1-like antigen comprises SEQ ID NO: 27.

10. The method of claim 9, wherein said histone H1-like antigen is in isolated form.

* * * * *

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
      (A) LENGTH: 212 amino acids
      (B) TYPE: amino acid
      (D) TOPOLOGY: linear (ix) FEATURE:
      (A) NAME/KEY: Peptide
      (B) LOCATION: 1..212
      (D) OTHER INFORMATION: /note= "product = Human Histone H1-S-1"

(xi) SEQUENCE DESCRIPTION: SEQ ID NO:1:

```
Ser Glu Thr Ala Pro Ala Ala Pro Ala Ala Ala Pro Pro Ala Glu Lys
 1               5                  10                  15

Ala Pro Val Lys Lys Lys Ala Ala Lys Lys Ala Gly Gly Thr Pro Arg
            20                  25                  30

Lys Ala Ser Gly Pro Pro Val Ser Glu Leu Ile Thr Lys Ala Val Ala
        35                  40                  45

Ala Ser Lys Glu Arg Ser Gly Val Ser Leu Ala Ala Leu Lys Lys Ala
    50                  55                  60

Leu Ala Ala Ala Gly Tyr Asp Val Glu Lys Asn Asn Ser Arg Ile Lys
65                  70                  75                  80

Leu Gly Leu Lys Ser Leu Val Ser Lys Gly Thr Leu Val Gln Thr Lys
                85                  90                  95

Gly Thr Gly Ala Ser Gly Ser Phe Lys Leu Asn Lys Lys Ala Ala Ser
            100                 105                 110

Gly Glu Ala Lys Pro Lys Val Lys Lys Ala Gly Gly Thr Lys Pro Lys
        115                 120                 125

Lys Pro Val Gly Ala Ala Lys Lys Pro Lys Lys Ala Ala Gly Gly Ala
    130                 135                 140

Thr Pro Lys Lys Ser Ala Lys Lys Thr Pro Lys Lys Ala Lys Lys Pro
145                 150                 155                 160

Ala Ala Ala Thr Val Thr Lys Lys Val Ala Lys Ser Pro Lys Lys Ala
                165                 170                 175
```

```
Lys Val Ala Lys Pro Lys Ala Ala Lys Ser Ala Ala Lys Ala Val
            180             185             190

Lys Pro Lys Ala Ala Lys Pro Val Val Pro Lys Lys Ala Ala
        195             200             205

Pro Lys Lys Lys
    210
```

(2) INFORMATION FOR SEQ ID NO:2:

(i) SEQUENCE CHARACTERISTICS:
        (A) LENGTH: 220 amino acids
        (B) TYPE: amino acid
        (D) TOPOLOGY: linear (ix) FEATURE:
        (A) NAME/KEY: Peptide
        (B) LOCATION: 1..220
        (D) OTHER INFORMATION: /note= "product = Human Histone
            H1-S-2"

(xi) SEQUENCE DESCRIPTION: SEQ ID NO:2:

```
Ser Glu Thr Ala Pro Leu Ala Pro Thr Ile Pro Ala Pro Ala Glu Lys
1               5                   10                  15

Thr Pro Val Lys Lys Lys Ala Lys Lys Ala Gly Ala Thr Ala Gly Lys
            20                  25                  30

Arg Lys Ala Ser Gly Pro Pro Val Ser Glu Leu Ile Thr Lys Ala Val
        35                  40                  45

Ala Ala Ser Lys Glu Arg Ser Gly Val Ser Leu Ala Ala Leu Lys Lys
    50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Thr Leu Val Gln Thr
                85                  90                  95

Lys Gly Thr Gly Ala Ser Gly Ser Phe Lys Leu Asn Lys Lys Ala Ala
            100                 105                 110

Ser Gly Glu Gly Lys Pro Lys Ala Lys Lys Ala Gly Ala Ala Lys Pro
        115                 120                 125

Arg Lys Pro Ala Gly Ala Ala Lys Lys Pro Lys Lys Val Ala Gly Ala
    130                 135                 140

Ala Thr Pro Lys Lys Ser Ile Lys Lys Thr Pro Lys Lys Val Lys Lys
145                 150                 155                 160

Pro Ala Thr Ala Ala Gly Thr Lys Val Ala Lys Ser Ala Lys Lys
                165                 170                 175

Val Lys Thr Pro Gln Pro Lys Lys Ala Ala Lys Ser Pro Ala Lys Ala
            180                 185                 190

Lys Ala Pro Lys Pro Lys Ala Ala Lys Pro Lys Ser Gly Lys Pro Lys
        195                 200                 205

Val Thr Lys Ala Lys Lys Ala Ala Pro Lys Lys Lys
    210                 215                 220
```

(2) INFORMATION FOR SEQ ID NO:3:

(i) SEQUENCE CHARACTERISTICS:
        (A) LENGTH: 222 amino acids
        (B) TYPE: amino acid
        (D) TOPOLOGY: linear (ix) FEATURE:
        (A) NAME/KEY: Peptide
        (B) LOCATION: 1..222

(D) OTHER INFORMATION: /note= "product = Human Histone H1-S-3"

(xi) SEQUENCE DESCRIPTION: SEQ ID NO:3:

```
Ser Glu Thr Ala Pro Ala Glu Thr Ala Thr Pro Ala Pro Val Glu Lys
  1               5                  10                  15

Ser Pro Ala Lys Lys Lys Ala Thr Lys Lys Ala Ala Gly Ala Gly Ala
             20                  25                  30

Ala Lys Arg Lys Ala Thr Gly Pro Pro Val Ser Glu Leu Ile Thr Lys
             35                  40                  45

Ala Val Ala Ala Ser Lys Glu Arg Asn Gly Leu Ser Leu Ala Ala Leu
 50                  55                  60

Lys Lys Ala Leu Ala Ala Gly Gly Tyr Asp Val Glu Lys Asn Asn Ser
 65                  70                  75                  80

Arg Ile Lys Leu Gly Leu Lys Ser Leu Val Ser Lys Gly Thr Leu Val
                 85                  90                  95

Gln Thr Lys Gly Thr Gly Ala Ser Gly Ser Phe Lys Leu Asn Lys Lys
                100                 105                 110

Ala Ala Ser Gly Glu Ala Lys Pro Lys Ala Lys Lys Ala Gly Ala Ala
            115                 120                 125

Lys Ala Lys Lys Pro Ala Gly Ala Thr Pro Lys Lys Ala Lys Lys Ala
130                 135                 140

Ala Gly Ala Lys Lys Ala Val Lys Lys Thr Pro Lys Lys Ala Lys Lys
145                 150                 155                 160

Pro Ala Ala Ala Gly Val Lys Val Ala Lys Ser Pro Lys Lys Ala
                165                 170                 175

Lys Ala Ala Ala Lys Pro Lys Lys Ala Thr Lys Ser Pro Ala Lys Pro
            180                 185                 190

Lys Ala Val Lys Pro Lys Ala Ala Lys Pro Lys Ala Ala Lys Pro Lys
            195                 200                 205

Ala Ala Lys Pro Lys Ala Lys Lys Ala Ala Lys Lys
            210                 215                 220
```

(2) INFORMATION FOR SEQ ID NO:4:

(i) SEQUENCE CHARACTERISTICS:
  (A) LENGTH: 218 amino acids
  (B) TYPE: amino acid
  (D) TOPOLOGY: linear (ix) FEATURE:
  (A) NAME/KEY: Peptide
  (B) LOCATION: 1..218
  (D) OTHER INFORMATION: /note= "product = Human Histone H1-S-4"

(xi) SEQUENCE DESCRIPTION: SEQ ID NO:4:

```
Ser Glu Thr Ala Pro Ala Ala Pro Ala Ala Pro Ala Pro Ala Glu Lys
  1               5                  10                  15

Thr Pro Val Lys Lys Lys Ala Arg Lys Ser Ala Gly Ala Ala Lys Arg
             20                  25                  30

Lys Ala Ser Gly Pro Pro Val Ser Glu Leu Ile Thr Lys Ala Val Ala
             35                  40                  45

Ala Ser Lys Glu Arg Ser Gly Val Ser Leu Ala Ala Leu Lys Lys Ala
 50                  55                  60

Leu Ala Ala Ala Gly Tyr Asp Val Glu Lys Asn Asn Ser Arg Ile Lys
 65                  70                  75                  80

Leu Gly Leu Lys Ser Leu Val Ser Lys Gly Thr Leu Val Gln Thr Lys
```

```
                    85                  90                  95
Gly Thr Gly Ala Ser Gly Ser Phe Lys Leu Asn Lys Ala Ala Ser
                100                 105                 110
Gly Glu Ala Lys Pro Lys Ala Lys Lys Ala Gly Ala Ala Lys Ala Lys
                115                 120                 125
Lys Pro Ala Gly Ala Ala Lys Lys Pro Lys Lys Ala Thr Gly Ala Ala
        130                 135                 140
Thr Pro Lys Lys Ser Ala Lys Lys Thr Pro Lys Lys Ala Lys Lys Pro
145                 150                 155                 160
Ala Ala Ala Ala Gly Ala Lys Lys Ala Lys Ser Pro Lys Lys Ala Lys
                165                 170                 175
Ala Ala Lys Pro Lys Lys Ala Pro Lys Ser Pro Ala Lys Ala Lys Ala
                180                 185                 190
Val Lys Pro Lys Ala Ala Lys Pro Lys Thr Ala Lys Pro Lys Ala Ala
                195                 200                 205
Lys Pro Lys Lys Ala Ala Lys Lys Lys
        210                 215
```

(2) INFORMATION FOR SEQ ID NO:5:

(i) SEQUENCE CHARACTERISTICS:
        (A) LENGTH: 193 amino acids
        (B) TYPE: amino acid
        (D) TOPOLOGY: linear (ix) FEATURE:
        (A) NAME/KEY: Peptide
        (B) LOCATION: 1..193
        (D) OTHER INFORMATION: /note= "product = Human Histone
           H1-o"

(xi) SEQUENCE DESCRIPTION: SEQ ID NO:5:

```
Thr Glu Asn Ser Thr Ser Ala Pro Ala Ala Lys Pro Lys Arg Ala Lys
1               5                   10                  15
Ala Ser Lys Lys Ser Thr Asp His Pro Lys Tyr Ser Asp Met Ile Val
                20                  25                  30
Ala Ala Ile Gln Ala Glu Lys Asn Arg Ala Gly Ser Ser Arg Gln Ser
            35                  40                  45
Ile Gln Lys Tyr Ile Lys Ser His Tyr Lys Val Gly Glu Asn Ala Asp
    50                  55                  60
Ser Gln Ile Lys Leu Ser Ile Lys Arg Leu Val Thr Thr Gly Val Leu
65                  70                  75                  80
Lys Gln Thr Lys Gly Val Gly Ala Ser Gly Ser Phe Arg Leu Ala Lys
                85                  90                  95
Ser Asp Glu Pro Lys Lys Ser Val Ala Phe Lys Lys Thr Lys Lys Glu
                100                 105                 110
Ile Lys Lys Val Ala Thr Pro Lys Lys Ala Ser Lys Pro Lys Lys Ala
                115                 120                 125
Ala Ser Lys Ala Pro Thr Lys Lys Pro Lys Ala Thr Pro Val Lys Lys
        130                 135                 140
Ala Lys Lys Lys Leu Ala Ala Thr Pro Lys Lys Ala Lys Lys Pro Lys
145                 150                 155                 160
Thr Val Lys Ala Lys Pro Val Lys Ala Ser Lys Pro Lys Lys Ala Lys
                165                 170                 175
Pro Val Lys Pro Lys Ala Lys Ser Ser Ala Lys Arg Ala Gly Lys Lys
                180                 185                 190
Lys
```

(2) INFORMATION FOR SEQ ID NO:6:

(i) SEQUENCE CHARACTERISTICS:
      (A) LENGTH: 206 amino acids
      (B) TYPE: amino acid
      (D) TOPOLOGY: linear (ix) FEATURE:
      (A) NAME/KEY: Peptide
      (B) LOCATION: 1..206
      (D) OTHER INFORMATION: /note= "product = Human Histone
          H1t"

(xi) SEQUENCE DESCRIPTION: SEQ ID NO:6:

Ser Glu Thr Val Pro Ala Ala Ser Ala Ser Ala Gly Val Ala Ala Met
1               5                   10                  15

Glu Lys Leu Pro Thr Lys Lys Arg Gly Arg Lys Pro Ala Gly Leu Ile
            20                  25                  30

Ser Ala Ser Arg Lys Val Pro Asn Leu Ser Val Ser Lys Leu Ile Thr
        35                  40                  45

Glu Ala Leu Ser Val Ser Gln Glu Arg Val Gly Met Ser Leu Val Ala
    50                  55                  60

Leu Lys Lys Ala Leu Ala Ala Gly Tyr Asp Val Glu Lys Asn Asn
65                  70                  75                  80

Ser Arg Ile Lys Leu Ser Leu Lys Ser Leu Val Asn Lys Gly Ile Leu
                85                  90                  95

Val Gln Thr Arg Gly Thr Gly Ala Ser Gly Ser Phe Lys Leu Ser Lys
            100                 105                 110

Lys Val Ile Pro Lys Ser Thr Arg Ser Lys Ala Lys Lys Ser Val Ser
            115                 120                 125

Ala Lys Thr Lys Lys Leu Val Leu Ser Arg Asp Ser Lys Ser Pro Lys
130                 135                 140

Thr Ala Lys Thr Asn Lys Arg Ala Lys Pro Arg Ala Thr Thr Pro
145                 150                 155                 160

Lys Thr Val Arg Ser Gly Arg Lys Ala Lys Gly Ala Lys Gly Lys Gln
                165                 170                 175

Lys Gln Lys Ser Pro Val Lys Ala Arg Ala Ser Lys Ser Lys Leu Thr
            180                 185                 190

Gln His His Glu Val Asn Val Arg Lys Ala Thr Ser Lys Lys
            195                 200                 205

(2) INFORMATION FOR SEQ ID NO:7:

(i) SEQUENCE CHARACTERISTICS:
      (A) LENGTH: 35 amino acids
      (B) TYPE: amino acid
      (D) TOPOLOGY: linear (xi) SEQUENCE DESCRIPTION: SEQ ID NO:7:

Ser Glu Thr Ala Pro Ala Glu Thr Ala Thr Pro Ala Pro Val Glu Lys
1               5                   10                  15

Ser Pro Ala Lys Lys Lys Ala Thr Lys Lys Ala Ala Gly Ala Gly Ala
            20                  25                  30

Ala Lys Arg
        35

(2) INFORMATION FOR SEQ ID NO:8:

(i) SEQUENCE CHARACTERISTICS:

(A) LENGTH: 699 base pairs
(B) TYPE: nucleic acid
(C) STRANDEDNESS: double
(D) TOPOLOGY: linear (ix) FEATURE:
(A) NAME/KEY: CDS
(B) LOCATION: 1..699

(ix) FEATURE:
(A) NAME/KEY: misc_feature
(B) LOCATION: 1..699
(D) OTHER INFORMATION: /note= "product = NANUC-2 heavy chain"

(xi) SEQUENCE DESCRIPTION: SEQ ID NO:8:

| | | | | | | | | | | | | | | | | |
|---|---|---|---|---|---|---|---|---|---|---|---|---|---|---|---|---|
| GCC | CAG | GTG | AAA | CTG | CTC | GAG | CAG | TCT | GGG | GGA | GGC | GTG | GTC | CAG | CCT | 48 |
| Ala | Gln | Val | Lys | Leu | Leu | Glu | Gln | Ser | Gly | Gly | Gly | Val | Val | Gln | Pro | |
| 1 | | | | 5 | | | | | 10 | | | | | 15 | | |
| GGG | AAG | TCC | CTG | AGA | CTC | TCC | TGT | GCA | GCC | TCT | GGA | TTC | ACC | TTC | AGG | 96 |
| Gly | Lys | Ser | Leu | Arg | Leu | Ser | Cys | Ala | Ala | Ser | Gly | Phe | Thr | Phe | Arg | |
| | | | 20 | | | | | 25 | | | | | 30 | | | |
| AAC | TAT | GGC | ATG | CAC | TGG | GTC | CGG | CAG | GCT | CCA | GGC | AAG | GGG | CTG | GAG | 144 |
| Asn | Tyr | Gly | Met | His | Trp | Val | Arg | Gln | Ala | Pro | Gly | Lys | Gly | Leu | Glu | |
| | | 35 | | | | | 40 | | | | | 45 | | | | |
| TGG | GTG | GCA | GGT | ATT | TCC | TCT | GAT | GGA | AGA | AAA | AAG | TAT | GTA | GAC | | 192 |
| Trp | Val | Ala | Gly | Ile | Ser | Ser | Asp | Gly | Arg | Lys | Lys | Tyr | Val | Asp | | |
| 50 | | | | | 55 | | | | | 60 | | | | | | |
| TCC | GTG | AAG | GGC | CGA | TTC | ACC | ATC | TCC | AGA | GAC | AAG | TCC | AAG | AAC | ACG | 240 |
| Ser | Val | Lys | Gly | Arg | Phe | Thr | Ile | Ser | Arg | Asp | Lys | Ser | Lys | Asn | Thr | |
| 65 | | | | | 70 | | | | | 75 | | | | | 80 | |
| CTG | TAT | CTG | CAA | ATG | AAC | AGC | CTC | AGA | GCT | GAG | GAC | ACG | GCT | GTG | TAT | 288 |
| Leu | Tyr | Leu | Gln | Met | Asn | Ser | Leu | Arg | Ala | Glu | Asp | Thr | Ala | Val | Tyr | |
| | | | | 85 | | | | | 90 | | | | | 95 | | |
| TAC | TGT | GCG | AAA | TTG | TCC | CGC | GCG | GGT | GGT | TTT | GAC | ATC | TGG | GGC | CAA | 336 |
| Tyr | Cys | Ala | Lys | Leu | Ser | Arg | Ala | Gly | Gly | Phe | Asp | Ile | Trp | Gly | Gln | |
| | | | 100 | | | | | 105 | | | | | 110 | | | |
| GGG | ACA | ATG | GTC | ACC | GTC | TCT | TCA | GCC | TCC | ACC | AAG | GGC | CCA | TCG | GTC | 384 |
| Gly | Thr | Met | Val | Thr | Val | Ser | Ser | Ala | Ser | Thr | Lys | Gly | Pro | Ser | Val | |
| | | 115 | | | | | 120 | | | | | 125 | | | | |
| TTT | CCC | CTG | GCA | CCC | TCC | TCC | AAG | AGC | ACC | TCT | GGG | GGC | ACA | GCG | GCC | 432 |
| Phe | Pro | Leu | Ala | Pro | Ser | Ser | Lys | Ser | Thr | Ser | Gly | Gly | Thr | Ala | Ala | |
| 130 | | | | | 135 | | | | | 140 | | | | | | |
| CTG | GGC | TGC | CTG | GTC | AAG | GAC | TAC | TTC | CCC | GAA | CCG | GTG | ACG | GTG | TCG | 480 |
| Leu | Gly | Cys | Leu | Val | Lys | Asp | Tyr | Phe | Pro | Glu | Pro | Val | Thr | Val | Ser | |
| 145 | | | | | 150 | | | | | 155 | | | | | 160 | |
| TGG | AAC | TCA | GGC | GCC | CTG | ACC | AGC | GGC | GTG | CAC | ACC | TTC | CCG | GCT | GTC | 528 |
| Trp | Asn | Ser | Gly | Ala | Leu | Thr | Ser | Gly | Val | His | Thr | Phe | Pro | Ala | Val | |
| | | | | 165 | | | | | 170 | | | | | 175 | | |
| CTA | CAG | TCC | TCA | GGA | CTC | TAC | TCC | CTC | AGC | AGC | GTG | GTG | ACC | GTG | CCC | 576 |
| Leu | Gln | Ser | Ser | Gly | Leu | Tyr | Ser | Leu | Ser | Ser | Val | Val | Thr | Val | Pro | |
| | | 180 | | | | | 185 | | | | | 190 | | | | |
| TCC | AGC | AGC | TTG | GGC | ACC | CAG | ACC | TAC | ATC | TGC | AAC | GTG | AAT | CAC | AAG | 624 |
| Ser | Ser | Ser | Leu | Gly | Thr | Gln | Thr | Tyr | Ile | Cys | Asn | Val | Asn | His | Lys | |
| | | 195 | | | | | 200 | | | | | 205 | | | | |
| CCC | AGC | AAC | ACC | AAG | GTG | GAC | AAG | AAA | GCA | GAG | CCC | AAA | TCT | TGT | GAC | 672 |
| Pro | Ser | Asn | Thr | Lys | Val | Asp | Lys | Lys | Ala | Glu | Pro | Lys | Ser | Cys | Asp | |
| | | 210 | | | | | 215 | | | | | 220 | | | | |
| AAA | ACT | AGT | CAC | CAC | CAC | CAC | CAC | CAC | | | | | | | | 699 |
| Lys | Thr | Ser | His | His | His | His | His | His | | | | | | | | |
| 225 | | | | 230 | | | | | | | | | | | | |

(2) INFORMATION FOR SEQ ID NO:9:

(i) SEQUENCE CHARACTERISTICS:
    (A) LENGTH: 233 amino acids
    (B) TYPE: amino acid
    (D) TOPOLOGY: linear (ii) MOLECULE TYPE: protein (xi) SEQUENCE DESCRIPTION: SEQ ID NO:9:

```
Ala Gln Val Lys Leu Leu Glu Gln Ser Gly Gly Val Val Gln Pro
 1               5                  10                  15

Gly Lys Ser Leu Arg Leu Ser Cys Ala Ala Ser Gly Phe Thr Phe Arg
                20                  25                  30

Asn Tyr Gly Met His Trp Val Arg Gln Ala Pro Gly Lys Gly Leu Glu
            35                  40                  45

Trp Val Ala Gly Ile Ser Ser Asp Gly Arg Lys Lys Tyr Val Asp
    50                  55                  60

Ser Val Lys Gly Arg Phe Thr Ile Ser Arg Asp Lys Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Lys Leu Ser Arg Ala Gly Gly Phe Asp Ile Trp Gly Gln
                100                 105                 110

Gly Thr Met Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Ala Glu Pro Lys Ser Cys Asp
    210                 215                 220

Lys Thr Ser His His His His His His
225                 230
```

(2) INFORMATION FOR SEQ ID NO:10:

(i) SEQUENCE CHARACTERISTICS:
    (A) LENGTH: 642 base pairs
    (B) TYPE: nucleic acid
    (C) STRANDEDNESS: double
    (D) TOPOLOGY: linear (ix) FEATURE:
    (A) NAME/KEY: CDS
    (B) LOCATION: 1..642

(ix) FEATURE:
    (A) NAME/KEY: misc_feature
    (B) LOCATION: 1..642
    (D) OTHER INFORMATION: /note= "product = NANUC-2 light chain"

(xi) SEQUENCE DESCRIPTION: SEQ ID NO:10:

```
GCC GAG CTC ACG CAG TCT CCA GGC ACC CTG TCT TTG TTT CCA GGG GAA    48
Ala Glu Leu Thr Gln Ser Pro Gly Thr Leu Ser Leu Phe Pro Gly Glu
 1               5                  10                  15
```

-continued

```
AGA GCC ACT CTC TCC TGC AGG GCC AGT CAG AGA ATT AGC ACC AGT TTC      96
Arg Ala Thr Leu Ser Cys Arg Ala Ser Gln Arg Ile Ser Thr Ser Phe
         20                  25                  30

TTA GCC TGG TAC CAG CAG AAG CCT GGC CAG TCT CCC AGG CTC CTC ATC     144
Leu Ala Trp Tyr Gln Gln Lys Pro Gly Gln Ser Pro Arg Leu Leu Ile
     35                  40                  45

TTT GAT GCA TCC ACC AGG GCC CCT GGC ATC CCT GAC AGG TTC AGT GCC     192
Phe Asp Ala Ser Thr Arg Ala Pro Gly Ile Pro Asp Arg Phe Ser Ala
 50                  55                  60

AGT TGG TCT GGG ACA GAC TTC ACT CTC ACC ATC AGC AGA CTG GAG CCT     240
Ser Trp Ser Gly Thr Asp Phe Thr Leu Thr Ile Ser Arg Leu Glu Pro
 65                  70                  75                  80

GAA GAT TTT GCA GTC TAT TAC TGT CAA CAT TAT GGT GGG TCT CCC TGG     288
Glu Asp Phe Ala Val Tyr Tyr Cys Gln His Tyr Gly Gly Ser Pro Trp
                 85                  90                  95

ACG TTC GGC CAA GGG ACC AAG GTG GAA ATC AAG CGA ACT GTG GCT GCA     336
Thr Phe Gly Gln Gly Thr Lys Val Glu Ile Lys Arg Thr Val Ala Ala
             100                 105                 110

CCA TCT GTC TTC ATC TTC CCG CCA TCT GAT GAG CAG TTG AAA TCT GGA     384
Pro Ser Val Phe Ile Phe Pro Pro Ser Asp Glu Gln Leu Lys Ser Gly
         115                 120                 125

ACT GCC TCT GTT GTG TGC CTG CTG AAT AAC TTC TAT CCC AGA GAG GCC     432
Thr Ala Ser Val Val Cys Leu Leu Asn Asn Phe Tyr Pro Arg Glu Ala
 130                 135                 140

AAA GTA CAG TGG AAG GTG GAT AAC GCC CTC CAA TCG GGT AAC TCC CAG     480
Lys Val Gln Trp Lys Val Asp Asn Ala Leu Gln Ser Gly Asn Ser Gln
145                 150                 155                 160

GAG AGT GTC ACA GAG CAG GAC AGC AAG GAC AGC ACC TAC AGC CTC AGC     528
Glu Ser Val Thr Glu Gln Asp Ser Lys Asp Ser Thr Tyr Ser Leu Ser
                 165                 170                 175

AGC ACC CTG ACG CTG AGC AAA GCA GAC TAC GAG AAA CAC AAA GTC TAC     576
Ser Thr Leu Thr Leu Ser Lys Ala Asp Tyr Glu Lys His Lys Val Tyr
             180                 185                 190

GCC TGC GAA GTC ACC CAT CAG GGC CTG AGC TCG CCC GTC ACA AAG AGC     624
Ala Cys Glu Val Thr His Gln Gly Leu Ser Ser Pro Val Thr Lys Ser
         195                 200                 205

TTC AAC AGG GGA GAG TGT                                             642
Phe Asn Arg Gly Glu Cys
     210
```

(2) INFORMATION FOR SEQ ID NO:11:

(i) SEQUENCE CHARACTERISTICS:
        (A) LENGTH: 214 amino acids
        (B) TYPE: amino acid
        (D) TOPOLOGY: linear (ii) MOLECULE TYPE: protein (xi) SEQUENCE DESCRIPTION: SEQ ID NO:11:

```
Ala Glu Leu Thr Gln Ser Pro Gly Thr Leu Ser Leu Phe Pro Gly Glu
 1               5                  10                  15

Arg Ala Thr Leu Ser Cys Arg Ala Ser Gln Arg Ile Ser Thr Ser Phe
         20                  25                  30

Leu Ala Trp Tyr Gln Gln Lys Pro Gly Gln Ser Pro Arg Leu Leu Ile
     35                  40                  45

Phe Asp Ala Ser Thr Arg Ala Pro Gly Ile Pro Asp Arg Phe Ser Ala
 50                  55                  60

Ser Trp Ser Gly Thr Asp Phe Thr Leu Thr Ile Ser Arg Leu Glu Pro
 65                  70                  75                  80
```

```
Glu Asp Phe Ala Val Tyr Tyr Cys Gln His Tyr Gly Gly Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210
```

(2) INFORMATION FOR SEQ ID NO:12:

(i) SEQUENCE CHARACTERISTICS:
        (A) LENGTH: 73 amino acids
        (B) TYPE: amino acid
        (D) TOPOLOGY: linear (xi) SEQUENCE DESCRIPTION: SEQ ID NO:12:

```
Ser Glu Thr Ala Pro Leu Ala Pro Thr Ile Pro Ala Pro Ala Glu Lys
1               5                   10                  15

Thr Pro Val Lys Lys Lys Ala Lys Lys Ala Gly Ala Thr Ala Gly Lys
            20                  25                  30

Arg Lys Ala Ser Gly Pro Pro Val Ser Glu Leu Ile Thr Lys Ala Val
            35                  40                  45

Ala Ala Ser Lys Glu Arg Ser Gly Val Ser Leu Ala Ala Leu Lys Lys
50                  55                  60

Ala Leu Ala Ala Ala Gly Tyr Asp Val
65                  70
```

(2) INFORMATION FOR SEQ ID NO:13:

(i) SEQUENCE CHARACTERISTICS:
        (A) LENGTH: 147 amino acids
        (B) TYPE: amino acid
        (D) TOPOLOGY: linear (xi) SEQUENCE DESCRIPTION: SEQ ID NO:13:

```
Glu Lys Asn Asn Ser Arg Ile Lys Leu Gly Leu Lys Ser Leu Val Ser
1               5                   10                  15

Lys Gly Thr Leu Val Gln Thr Lys Gly Thr Gly Ala Ser Gly Ser Phe
            20                  25                  30

Lys Leu Asn Lys Lys Ala Ala Ser Gly Glu Gly Lys Pro Lys Ala Lys
            35                  40                  45

Lys Ala Gly Ala Ala Lys Pro Arg Lys Pro Ala Gly Ala Ala Lys Lys
            50                  55                  60

Pro Lys Lys Val Ala Gly Ala Ala Thr Pro Lys Lys Ser Ile Lys Lys
65                  70                  75                  80

Thr Pro Lys Lys Val Lys Lys Pro Ala Thr Ala Ala Gly Thr Lys Lys
```

```
                        85                  90                      95
Val Ala Lys Ser Ala Lys Lys Val Lys Thr Pro Gln Pro Lys Lys Ala
                100                 105                 110

Ala Lys Ser Pro Ala Lys Ala Lys Ala Pro Lys Pro Lys Ala Ala Lys
                115                 120                 125

Pro Lys Ser Gly Lys Pro Lys Val Thr Lys Ala Lys Lys Ala Ala Pro
        130                 135                 140

Lys Lys Lys
145

(2) INFORMATION FOR SEQ ID NO:14:

(i) SEQUENCE CHARACTERISTICS:
        (A) LENGTH: 113 amino acids
        (B) TYPE: amino acid
        (D) TOPOLOGY: linear (xi) SEQUENCE DESCRIPTION: SEQ ID NO:14:

Asn Lys Lys Ala Ala Ser Gly Glu Gly Lys Pro Lys Ala Lys Lys Ala
1               5                   10                  15

Gly Ala Ala Lys Pro Arg Lys Pro Ala Gly Ala Ala Lys Lys Pro Lys
                20                  25                  30

Lys Val Ala Gly Ala Ala Thr Pro Lys Lys Ser Ile Lys Lys Thr Pro
            35                  40                  45

Lys Lys Val Lys Pro Ala Thr Ala Ala Gly Thr Lys Lys Val Ala
        50                  55                  60

Lys Ser Ala Lys Lys Val Lys Thr Pro Gln Pro Lys Lys Ala Ala Lys
65                  70                  75                  80

Ser Pro Ala Lys Ala Lys Ala Pro Lys Pro Lys Ala Ala Lys Pro Lys
                85                  90                  95

Ser Gly Lys Pro Lys Val Thr Lys Ala Lys Lys Ala Ala Pro Lys Lys
            100                 105                 110

Lys (2) INFORMATION FOR SEQ ID NO:15:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:15:

Phe Lys Leu Asn Lys Lys Ala Ala Ser Gly Glu Ala Lys Pro Lys
1               5                   10                  15

(2) INFORMATION FOR SEQ ID NO:16:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:16:

Glu Ala Lys Pro Lys Val Lys Lys Ala Gly Gly Thr Lys Pro Lys
1               5                   10                  15

(2) INFORMATION FOR SEQ ID NO:17:

(i) SEQUENCE CHARACTERISTICS:
        (A) LENGTH: 15 amino acids
        (B) TYPE: amino acid
```

(D) TOPOLOGY: linear (xi) SEQUENCE DESCRIPTION: SEQ ID NO:17:

Gly Thr Lys Pro Lys Lys Pro Val Gly Ala Ala Lys Lys Pro Lys
1               5                   10                  15

(2) INFORMATION FOR SEQ ID NO:18:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:18:

Ala Lys Lys Pro Lys Lys Ala Ala Gly Gly Ala Thr Pro Lys Lys
1               5                   10                  15

(2) INFORMATION FOR SEQ ID NO:19:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:19:

Ala Thr Pro Lys Lys Ser Ala Lys Lys Thr Pro Lys Lys Ala Lys
1               5                   10                  15

(2) INFORMATION FOR SEQ ID NO:20:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:20:

Pro Lys Lys Ala Lys Lys Pro Ala Ala Ala Thr Val Thr Lys Lys
1               5                   10                  15

(2) INFORMATION FOR SEQ ID NO:21:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:21:

Thr Val Thr Lys Lys Val Ala Lys Ser Pro Lys Lys Ala Lys Val
1               5                   10                  15

(2) INFORMATION FOR SEQ ID NO:22:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:22:

Lys Lys Ala Lys Val Ala Lys Pro Lys Lys Ala Ala Lys Ser Ala
1               5                   10                  15

(2) INFORMATION FOR SEQ ID NO:23:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:23:

Ala Ala Lys Ser Ala Ala Lys Ala Val Lys Pro Lys Ala Ala Lys
1               5                   10                  15

(2) INFORMATION FOR SEQ ID NO:24:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:24:

Pro Lys Ala Ala Lys Pro Lys Val Val Lys Pro Lys Lys Ala Ala
1               5                   10                  15

(2) INFORMATION FOR SEQ ID NO:25:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:25:

Lys Pro Lys Val Val Lys Pro Lys Lys Ala Ala Pro Lys Lys Lys
1               5                   10                  15

(2) INFORMATION FOR SEQ ID NO:26:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:26:

Lys Pro Ala Ala Ala
1               5

(2) INFORMATION FOR SEQ ID NO:27:

(i) SEQUENCE CHARACTERISTICS:
        (A) LENGTH: 214 amino acids
        (B) TYPE: amino acid
        (D) TOPOLOGY: linear (ii) MOLECULE TYPE: peptide (xi) SEQUENCE DESCRIPTION: SEQ ID NO:27:

Met Asn Lys Ala Glu Leu Ile Asp Val Leu Thr Gln Lys Leu Gly Ser
1               5                   10                  15

Asp Arg Arg Gln Ala Thr Ala Ala Val Glu Asn Val Val Asp Thr Ile
                20                  25                  30

Val Arg Ala Val His Lys Gly Asp Ser Val Thr Ile Thr Gly Phe Gly
            35                  40                  45

Val Phe Glu Gln Arg Arg Arg Ala Ala Arg Val Ala Arg Asn Pro Arg
        50                  55                  60

Thr Gly Glu Thr Val Lys Val Lys Pro Thr Ser Val Pro Ala Phe Arg
65                  70                  75                  80

Pro Gly Ala Gln Phe Lys Ala Val Val Ser Gly Ala Gln Arg Leu Pro
                85                  90                  95

Ala Glu Gly Pro Ala Val Lys Arg Gly Val Gly Ala Ser Ala Ala Lys
            100                 105                 110

Lys Val Ala Lys Lys Ala Pro Ala Lys Lys Ala Thr Lys Ala Ala Lys

```
                    115                 120                 125
Lys Ala Ala Thr Lys Ala Pro Ala Arg Lys Ala Ala Thr Lys Ala Pro
    130                 135                 140

Ala Lys Lys Ala Ala Thr Lys Ala Pro Ala Lys Lys Ala Val Lys Ala
145                 150                 155                 160

Thr Lys Ser Pro Ala Lys Lys Val Thr Lys Ala Val Lys Lys Thr Ala
                165                 170                 175

Val Lys Ala Ser Val Arg Lys Ala Ala Thr Lys Ala Pro Ala Lys Lys
            180                 185                 190

Ala Ala Ala Lys Arg Pro Ala Thr Lys Ala Pro Ala Lys Lys Ala Thr
        195                 200                 205

Ala Arg Arg Gly Arg Lys
    210
```

(2) INFORMATION FOR SEQ ID NO:28:

(i) SEQUENCE CHARACTERISTICS:
        (A) LENGTH: 323 amino acids
        (B) TYPE: amino acid
        (D) TOPOLOGY: linear (ii) MOLECULE TYPE: peptide (xi) SEQUENCE DESCRIPTION: SEQ ID NO:28:

```
Met Lys Ser Lys Val Leu Ala Leu Leu Ile Pro Ala Leu Leu Ala Ala
1               5                   10                  15

Gly Ala Ala His Ala Ala Glu Val Tyr Asn Lys Asp Gly Asn Lys Leu
                20                  25                  30

Asp Leu Tyr Gly Lys Val Asp Gly Leu His Tyr Phe Ser Asp Asn Ser
            35                  40                  45

Ala Lys Asp Gly Asp Gln Ser Tyr Ala Arg Leu Gly Phe Lys Gly Glu
        50                  55                  60

Thr Gln Ile Asn Asp Gln Leu Thr Gly Tyr Gly Gln Trp Glu Tyr Asn
65                  70                  75                  80

Ile Gln Ala Asn Asn Thr Glu Ser Ser Lys Asn Gln Ser Trp Thr Arg
                85                  90                  95

Leu Ala Phe Ala Gly Leu Lys Phe Ala Asp Tyr Gly Ser Phe Asp Tyr
            100                 105                 110

Gly Arg Asn Tyr Gly Val Met Tyr Asp Ile Glu Gly Trp Thr Asp Met
        115                 120                 125

Leu Pro Glu Phe Gly Gly Asp Ser Tyr Thr Asn Ala Asp Asn Phe Met
    130                 135                 140

Thr Gly Arg Ala Asn Gly Val Ala Thr Tyr Arg Asn Thr Asp Phe Phe
145                 150                 155                 160

Gly Leu Val Asn Gly Leu Asn Phe Ala Val Gln Tyr Gln Gly Asn Asn
                165                 170                 175

Glu Gly Ala Ser Asn Gly Gln Glu Gly Thr Asn Asn Gly Arg Asp Val
            180                 185                 190

Arg His Glu Asn Gly Asp Gly Trp Gly Leu Ser Thr Thr Tyr Asp Leu
        195                 200                 205

Gly Met Gly Phe Ser Ala Gly Ala Ala Tyr Thr Ser Ser Asp Arg Thr
    210                 215                 220

Asn Asp Gln Val Asn His Thr Ala Ala Gly Gly Asp Lys Ala Asp Ala
225                 230                 235                 240

Trp Thr Ala Gly Leu Lys Tyr Asp Ala Asn Asn Ile Tyr Leu Ala Thr
                245                 250                 255
```

```
Met Tyr Ser Glu Thr Arg Asn Met Thr Pro Phe Gly Asp Ser Asp Tyr
            260                 265                 270

Ala Val Ala Asn Lys Thr Gln Asn Phe Glu Val Thr Ala Gly Tyr Gln
            275                 280                 285

Phe Asp Phe Gly Leu Arg Pro Ala Val Ser Phe Leu Met Ser Lys Gly
            290                 295                 300

Arg Asp Leu His Ala Ala Gly Gly Ala Asp Asn Pro Ala Gly Val Asp
305                 310                 315                 320

Asp Lys Asp (2) INFORMATION FOR SEQ ID NO:29:

(i) SEQUENCE CHARACTERISTICS:
        (A) LENGTH: 377 amino acids
        (B) TYPE: amino acid
        (D) TOPOLOGY: linear (ii) MOLECULE TYPE: peptide (xi) SEQUENCE DESCRIPTION: SEQ ID NO:29:

Met Lys Ser Lys Val Leu Ala Leu Leu Ile Pro Ala Leu Leu Ala Ala
1               5                   10                  15

Gly Ala Ala His Ala Ala Glu Val Tyr Asn Lys Asp Gly Asn Lys Leu
            20                  25                  30

Asp Leu Tyr Gly Lys Val Asp Gly Leu His Tyr Phe Ser Asp Asn Ser
            35                  40                  45

Ala Lys Asp Gly Asp Gln Ser Tyr Ala Arg Leu Gly Phe Lys Gly Glu
            50                  55                  60

Thr Gln Ile Asn Asp Gln Leu Thr Gly Tyr Gln Gln Trp Glu Tyr Asn
65                  70                  75                  80

Ile Gln Ala Asn Asn Thr Glu Ser Ser Lys Asn Gln Ser Trp Thr Arg
                85                  90                  95

Leu Ala Phe Ala Gly Leu Lys Phe Ala Asp Tyr Gly Ser Phe Asp Tyr
            100                 105                 110

Gly Arg Asn Tyr Gly Val Met Tyr Asp Ile Glu Gly Trp Thr Asp Met
            115                 120                 125

Leu Pro Glu Phe Gly Gly Asp Ser Tyr Thr Asn Ala Asp Asn Phe Met
            130                 135                 140

Thr Gly Arg Ala Asn Gly Val Ala Thr Tyr Arg Asn Thr Asp Phe Phe
145                 150                 155                 160

Gly Leu Val Asn Gly Leu Asn Phe Ala Val Gln Tyr Gln Gly Asn Asn
                165                 170                 175

Glu Gly Ala Ser Asn Gly Gln Glu Gly Thr Asn Asn Gly Arg Asp Val
            180                 185                 190

Arg His Glu Asn Gly Asp Gly Trp Gly Leu Ser Thr Thr Tyr Asp Leu
            195                 200                 205

Gly Met Gly Phe Ser Ala Gly Ala Ala Tyr Thr Ser Ser Asp Arg Thr
            210                 215                 220

Asn Asp Gln Val Asn His Thr Ala Ala Gly Gly Asp Lys Ala Asp Ala
225                 230                 235                 240

Trp Thr Ala Gly Leu Lys Tyr Asp Ala Asn Asn Ile Tyr Leu Ala Thr
                245                 250                 255

Met Tyr Ser Glu Thr Arg Asn Met Thr Pro Phe Gly Asp Ser Asp Tyr
            260                 265                 270

Ala Val Ala Asn Lys Thr Gln Asn Phe Glu Val Thr Ala Gln Tyr Gln
```

-continued

```
                 275                 280                 285
Phe Asp Phe Gly Leu Arg Pro Ala Val Ser Phe Leu Met Ser Lys Gly
    290                 295                 300
Arg Asp Leu His Ala Ala Gly Gly Ala Asp Asn Pro Ala Gly Val Asp
305                 310                 315                 320
Asp Lys Asp Leu Val Lys Tyr Ala Asp Ile Gly Ala Thr Tyr Tyr Phe
                325                 330                 335
Asn Lys Asn Met Ser Thr Tyr Val Asp Tyr Lys Ile Asn Leu Ile Asp
                340                 345                 350
Glu Asp Asp Ser Phe Tyr Ala Ala Asn Gly Ile Ser Thr Asp Asp Ile
                355                 360                 365
Val Ala Leu Gly Leu Val Tyr Gln Phe
    370                 375

(2) INFORMATION FOR SEQ ID NO:30:

(i) SEQUENCE CHARACTERISTICS:
        (A) LENGTH: 367 amino acids
        (B) TYPE: amino acid
        (D) TOPOLOGY: linear (ii) MOLECULE TYPE: peptide (xi) SEQUENCE DESCRIPTION: SEQ ID NO:30:

Met Lys Val Lys Val Leu Ser Leu Leu Val Pro Ala Leu Leu Val Ala
1               5                   10                  15
Gly Ala Ala Asn Ala Ala Glu Val Tyr Asn Lys Asp Gly Asn Lys Leu
                20                  25                  30
Asp Leu Tyr Gly Lys Val Asp Gly Leu His Tyr Phe Ser Asp Asn Lys
            35                  40                  45
Asp Val Asp Gly Asp Gln Thr Tyr Met Arg Leu Gly Phe Lys Gly Glu
        50                  55                  60
Thr Gln Val Thr Asp Gln Leu Thr Gly Tyr Gly Gln Trp Glu Tyr Gln
65                  70                  75                  80
Ile Gln Gly Asn Ser Ala Glu Asn Glu Asn Asn Ser Trp Thr Arg Val
                85                  90                  95
Ala Phe Ala Gly Leu Lys Phe Gln Asp Val Gly Ser Phe Asp Tyr Gly
                100                 105                 110
Arg Asn Tyr Gly Val Val Tyr Asp Val Thr Ser Trp Thr Asp Val Leu
            115                 120                 125
Pro Glu Phe Gly Gly Asp Thr Tyr Gly Ser Asp Asn Phe Met Gln Gln
    130                 135                 140
Arg Gly Asn Gly Phe Ala Thr Tyr Arg Asn Thr Asp Phe Phe Gly Leu
145                 150                 155                 160
Val Asp Gly Leu Asn Phe Ala Val Gln Tyr Gln Gly Lys Asn Gly Asn
                165                 170                 175
Pro Ser Gly Glu Gly Phe Thr Ser Gly Val Thr Asn Asn Gly Arg Asp
                180                 185                 190
Ala Leu Arg Gln Asn Gly Asp Gly Val Gly Gly Ser Ile Thr Tyr Asp
            195                 200                 205
Tyr Glu Gly Phe Gly Ile Gly Gly Ala Ile Ser Ser Ser Lys Arg Thr
        210                 215                 220
Asp Ala Gln Asn Thr Ala Ala Tyr Ile Gly Asn Gly Asp Arg Ala Glu
225                 230                 235                 240
Thr Tyr Thr Gly Gly Leu Lys Tyr Asp Ala Asn Asn Ile Tyr Leu Ala
                245                 250                 255
```

```
Ala Gln Tyr Thr Gln Thr Tyr Asn Ala Thr Arg Val Gly Ser Leu Gly
            260                 265                 270

Trp Ala Asn Lys Ala Gln Asn Phe Glu Ala Val Ala Gln Tyr Gln Phe
            275                 280                 285

Asp Phe Gly Leu Arg Pro Ser Leu Ala Tyr Leu Gln Ser Lys Gly Lys
            290                 295                 300

Asn Leu Gly Arg Gly Tyr Asp Asp Glu Asp Ile Leu Lys Tyr Val Asp
305                 310                 315                 320

Val Gly Ala Thr Tyr Tyr Phe Asn Lys Asn Met Ser Thr Tyr Val Asp
                325                 330                 335

Tyr Lys Ile Asn Leu Leu Asp Asp Asn Gln Phe Thr Arg Asp Ala Gly
            340                 345                 350

Ile Asn Thr Asp Asn Ile Val Ala Leu Gly Leu Val Tyr Gln Phe
            355                 360                 365

(2) INFORMATION FOR SEQ ID NO:31:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:31:

Met Asn Lys Ala Glu Leu Ile Asp Val Leu Thr Thr Lys Met Xaa Ser
1               5                   10                  15

Asp Arg Arg Gln Xaa Thr Ala Xaa Val Glu Asp
            20                  25

(2) INFORMATION FOR SEQ ID NO:32:

(i) SEQUENCE CHARACTERISTICS:
        (A) LENGTH: 226 amino acids
        (B) TYPE: amino acid
        (D) TOPOLOGY: linear (ii) MOLECULE TYPE: peptide (xi) SEQUENCE DESCRIPTION: SEQ ID NO:32:

Met Ser Glu Thr Ala Pro Ala Glu Thr Ala Thr Pro Ala Pro Val Glu
1               5                   10                  15

Lys Ser Pro Ala Lys Lys Lys Ala Thr Lys Ala Ala Gly Ala Gly
            20                  25                  30

Ala Ala Lys Arg Lys Ala Thr Gly Pro Pro Val Ser Glu Leu Ile Thr
            35                  40                  45

Lys Ala Val Ala Ala Ser Lys Glu Arg Asn Gly Leu Ser Leu Ala Ala
        50                  55                  60

Leu Lys Lys Ala Leu Ala Ala Gly Gly Tyr Asp Val Glu Lys Asn Asn
65                  70                  75                  80

Ser Arg Ile Lys Leu Gly Leu Lys Ser Leu Val Ser Lys Gly Thr Leu
            85                  90                  95

Val Gln Thr Lys Gly Thr Gly Ala Ser Gly Ser Phe Lys Leu Asn Lys
            100                 105                 110

Lys Ala Ala Ser Gly Glu Ala Lys Pro Lys Ala Lys Lys Ala Gly Ala
            115                 120                 125

Ala Lys Ala Lys Lys Pro Ala Gly Ala Thr Pro Lys Lys Ala Lys Lys
            130                 135                 140
```

```
Ala Ala Gly Ala Lys Lys Ala Val Lys Lys Thr Pro Lys Lys Ala Lys
145                 150                 155                 160

Lys Pro Ala Ala Ala Gly Val Lys Lys Val Ala Lys Ser Pro Lys Lys
                165                 170                 175

Ala Lys Ala Ala Ala Lys Pro Lys Lys Ala Thr Lys Ser Pro Ala Lys
                180                 185                 190

Pro Lys Ala Val Lys Pro Lys Ala Ala Lys Pro Lys Ala Ala Lys Pro
        195                 200                 205

Lys Ala Ala Lys Pro Lys Ala Ala Lys Ala Lys Lys Ala Ala Ala Lys
        210                 215                 220

Lys Lys
225
```

(2) INFORMATION FOR SEQ ID NO:33:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:33:

```
Ala Glu Val Tyr Asn Lys Asp Gly Asn Lys Leu Asp Leu Tyr Gly Lys
1               5                   10                  15

Val Asp Gly
```

(2) INFORMATION FOR SEQ ID NO:34:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:34:

```
Lys Lys Pro Ala Ala Ala Gly Val Lys Lys Val Ala Lys Ser Pro
1               5                   10                  15
```

(2) INFORMATION FOR SEQ ID NO:35:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:35:

```
Val Ala Lys Ser Pro Lys Lys Ala Lys Ala Ala Lys Pro Lys
1               5                   10                  15
```

(2) INFORMATION FOR SEQ ID NO:36:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:36:

```
Ala Ala Lys Pro Lys Lys Ala Thr Lys Ser Pro Ala Lys Pro Lys
1               5                   10                  15
```

(2) INFORMATION FOR SEQ ID NO:37:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:37:

```
Lys Ser Pro Lys Lys Ala Lys Ala Ala Ala Lys Pro Lys
1               5                   10
```

(2) INFORMATION FOR SEQ ID NO:38:

(i) SEQUENCE CHARACTERISTICS:
        (A) LENGTH: 116 amino acids
        (B) TYPE: amino acid
        (D) TOPOLOGY: linear (ii) MOLECULE TYPE: peptide (xi) SEQUENCE DESCRIPTION: SEQ ID NO:38:

```
Leu Ala Ala Gly Gly Tyr Asp Val Glu Lys Asn Asn Ser Arg Ile Lys
1               5                   10                  15

Leu Gly Leu Lys Ser Leu Val Ser Lys Gly Thr Leu Val Gln Thr Lys
            20                  25                  30

Gly Thr Gly Ala Ser Gly Ser Phe Lys Leu Asn Lys Lys Ala Ala Ser
            35                  40                  45

Gly Glu Ala Lys Pro Lys Ala Lys Lys Ala Gly Ala Ala Lys Ala Lys
        50                  55                  60

Lys Pro Ala Gly Ala Thr Pro Lys Lys Ala Lys Lys Ala Ala Gly Ala
65                  70                  75                  80

Lys Lys Ala Val Lys Lys Thr Pro Lys Lys Ala Lys Lys Pro Ala Ala
                85                  90                  95

Ala Gly Val Lys Lys Val Ala Lys Ser Pro Lys Lys Ala Lys Ala Ala
            100                 105                 110

Ala Lys Pro Lys
        115
```

(2) INFORMATION FOR SEQ ID NO:39:

(i) SEQUENCE CHARACTERISTICS:
        (A) LENGTH: 103 amino acids
        (B) TYPE: amino acid
        (D) TOPOLOGY: linear (ii) MOLECULE TYPE: peptide (xi) SEQUENCE DESCRIPTION: SEQ ID NO:39:

```
Leu Ala Ala Gly Gly Tyr Asp Val Glu Lys Asn Asn Ser Arg Ile Lys
1               5                   10                  15

Leu Gly Leu Lys Ser Leu Val Ser Lys Gly Thr Leu Val Gln Thr Lys
            20                  25                  30

Gly Thr Gly Ala Ser Gly Ser Phe Lys Leu Asn Lys Lys Ala Ala Ser
            35                  40                  45

Gly Glu Ala Lys Pro Lys Ala Lys Lys Ala Gly Ala Ala Lys Ala Lys
        50                  55                  60

Lys Pro Ala Gly Ala Thr Pro Lys Lys Ala Lys Lys Ala Ala Gly Ala
65                  70                  75                  80
```

```
Lys Lys Ala Val Lys Lys Thr Pro Lys Lys Ala Lys Lys Pro Ala Ala
                85                  90                  95

Ala Gly Val Lys Lys Val Ala
            100
```

(2) INFORMATION FOR SEQ ID NO:40:

(i) SEQUENCE CHARACTERISTICS:
        (A) LENGTH: 158 amino acids
        (B) TYPE: amino acid
        (D) TOPOLOGY: linear (ii) MOLECULE TYPE: peptide (xi) SEQUENCE DESCRIPTION: SEQ ID NO:40:

```
Leu Ala Ala Gly Gly Tyr Asp Val Glu Lys Asn Asn Ser Arg Ile Lys
1               5                   10                  15

Leu Gly Leu Lys Ser Leu Val Ser Lys Gly Thr Leu Val Gln Thr Lys
                20                  25                  30

Gly Thr Gly Ala Ser Gly Ser Phe Lys Leu Asn Lys Lys Ala Ala Ser
                35                  40                  45

Gly Glu Ala Lys Pro Lys Ala Lys Ala Gly Ala Ala Lys Ala Lys Lys
        50                  55                  60

Lys Pro Ala Gly Ala Thr Pro Lys Lys Ala Lys Lys Ala Ala Gly Ala
65                  70                  75                  80

Lys Lys Ala Val Lys Lys Thr Pro Lys Lys Ala Lys Lys Pro Ala Ala
                85                  90                  95

Ala Gly Val Lys Lys Val Ala Lys Ser Pro Lys Lys Ala Lys Ala Ala
            100                 105                 110

Ala Lys Pro Lys Lys Ala Thr Lys Ser Pro Ala Lys Pro Lys Ala Val
            115                 120                 125

Lys Pro Lys Ala Ala Lys Pro Lys Ala Ala Lys Pro Lys Ala Ala Lys
        130                 135                 140

Pro Lys Ala Ala Lys Ala Lys Lys Ala Ala Lys Lys Lys
145                 150                 155
```

(2) INFORMATION FOR SEQ ID NO:41:

(i) SEQUENCE CHARACTERISTICS:
        (A) LENGTH: 55 amino acids
        (B) TYPE: amino acid
        (D) TOPOLOGY: linear (ii) MOLECULE TYPE: peptide (xi) SEQUENCE DESCRIPTION: SEQ ID NO:41:

```
Lys Ser Pro Lys Lys Ala Lys Ala Ala Ala Lys Pro Lys Lys Ala Thr
1               5                   10                  15

Lys Ser Pro Ala Lys Pro Lys Ala Val Lys Pro Lys Ala Ala Lys Pro
                20                  25                  30

Lys Ala Ala Lys Pro Lys Ala Ala Lys Pro Lys Ala Ala Lys Ala Lys
                35                  40                  45

Lys Ala Ala Ala Lys Lys Lys
        50                  55
```